US012667282B2

(12) United States Patent
Ekchian et al.

(10) Patent No.: US 12,667,282 B2
(45) Date of Patent: Jun. 30, 2026

(54) METHODS AND SYSTEMS FOR QUANTITATIVE MONITORING OF IN VIVO TUMOR OXYGENATION

(71) Applicants:Massachusetts Institute of Technology, Cambridge, MA (US); The Brigham and Women's Hospital, Inc., Boston, MA (US)

(72) Inventors: Gregory James Ekchian, Belmont, MA (US); Michael J. Cima, Winchester, MA (US); Robert Cormack, Milton, MA (US); Larissa Lee, Newton, MA (US); Ehud Jeruham Schmidt, Newton, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 555 days.

(21) Appl. No.: 16/490,634

(22) PCT Filed: Mar. 3, 2018

(86) PCT No.: PCT/US2018/020810
§ 371 (c)(1),
(2) Date: Sep. 3, 2019

(87) PCT Pub. No.: WO2018/161061
PCT Pub. Date: Sep. 7, 2018

(65) Prior Publication Data
US 2020/0000382 A1 Jan. 2, 2020

Related U.S. Application Data

(60) Provisional application No. 62/466,615, filed on Mar. 3, 2017.

(51) Int. Cl.
A61B 5/145 (2006.01)
A61B 5/00 (2006.01)
(Continued)

(52) U.S. Cl.
CPC ........ *A61B 5/14503* (2013.01); *A61B 5/1473* (2013.01); *A61B 5/6852* (2013.01);
(Continued)

(58) Field of Classification Search
CPC ... A61B 5/14503; A61B 5/055; A61B 5/1473; A61B 5/6852; A61N 5/1001;
(Continued)

(56) References Cited

U.S. PATENT DOCUMENTS 5,389,217 A * 2/1995 Singer ................. A61B 5/6853
204/415
5,462,053 A * 10/1995 Briggs ............... A61K 49/1806
424/9.322

(Continued)

FOREIGN PATENT DOCUMENTS

WO 2011/140193 A1 11/2011
WO WO-2012127455 A1 * 9/2012 .......... A61N 5/1001
WO 2012/158812 A1 11/2012

OTHER PUBLICATIONS

PCT International Search Report and Written Opinion for PCT Application No. PCT/US2018/020810 mailed Jul. 9, 2018 (17 pages).

(Continued)

*Primary Examiner* — Charles A Marmor, II
*Assistant Examiner* — Meghan R Kumar
(74) *Attorney, Agent, or Firm* — Eversheds Sutherland (US) LLP

(57) ABSTRACT
An oxygen sensor is provided for measuring a dissolved oxygen concentration when deployed or implanted at a
(Continued)

tissue site. The oxygen sensor includes a solid-state contrast agent for oxygen. The oxygen sensor is configured to indicate the dissolved oxygen concentration of a tissue when subjected to a magnetic resonance based method. The oxygen sensor may be used to map tumor oxygenation levels and for adaptive planning in brachytherapy.

19 Claims, 10 Drawing Sheets

(51) Int. Cl.

| | |
|---|---|
| *A61B 5/055* | (2006.01) |
| *A61B 5/1473* | (2006.01) |
| *A61N 5/10* | (2006.01) |
| *G01R 33/28* | (2006.01) |
| *G01R 33/50* | (2006.01) |
| *G01R 33/56* | (2006.01) |

(52) U.S. Cl.
CPC ......... *A61N 5/1001* (2013.01); *A61N 5/1038* (2013.01); *G01R 33/285* (2013.01); *G01R 33/50* (2013.01); *G01R 33/5601* (2013.01)

(58) Field of Classification Search
CPC .... A61N 5/1038; G01R 33/285; G01R 33/50; G01R 33/5601
See application file for complete search history.

(56) References Cited

U.S. PATENT DOCUMENTS

| | | | |
|---|---|---|---|
| 5,498,421 | A | 3/1996 | Grinstaff et al. |
| 6,171,240 | B1 | 1/2001 | Young et al. |
| 6,256,522 | B1 | 7/2001 | Schultz |
| 6,589,506 | B2 | 7/2003 | Cremillieux et al. |
| 7,354,391 | B2 | 4/2008 | Stubbs |
| 9,044,179 | B2 | 6/2015 | Wilson et al. |
| 2003/0199687 | A1 | 10/2003 | Yalpani |
| 2006/0177379 | A1 | 8/2006 | Asgari |
| 2007/0135698 | A1 | 6/2007 | Shah et al. |
| 2010/0239679 | A1 | 9/2010 | Greene et al. |
| 2010/0287887 | A1 | 11/2010 | Bolan et al. |
| 2011/0288234 | A1 | 11/2011 | Pandey et al. |
| 2013/0046164 | A1* | 2/2013 | Liu .................... A61B 5/14503 600/364 |
| 2014/0128720 | A1 | 5/2014 | Gallez et al. |
| 2014/0155684 | A1* | 6/2014 | Ehrenreich ..... A61M 25/10184 604/509 |
| 2014/0178297 | A1 | 6/2014 | Frank et al. |
| 2016/0030768 | A1 | 2/2016 | Ennis et al. |
| 2016/0199668 | A1* | 7/2016 | Bharat ................ A61N 5/1007 600/3 |

OTHER PUBLICATIONS

Akoka et al., "Concentration Measurement by Proton NMR Using the ERETIC Method," Analytical Chemistry, 1999, 71(13):2554-2557.
Cochran, "Investigating Escape of Low MW Siloxanes from PDMS Matrix in Aqueous Solution," 2013, https://dspace.mit.edu/bitstream/handle/1721.1/81140/858281935-MIT.pdf?sequence=2.
Diepart et al., "In Vivo Mapping of Tumor Oxygen Consumption Using 19F MRI Relaxometry," NMR Biomed., 2011, 24:458-463.
Hallac et al., Correlations of Nonivasive BOLD and TOLD MRI with pO2 and Relevance to Tumor Radiation Response, Magnetic Resonance in Medicine, 2014, 71:1863-1873.
Kodibagkar et al., "Novel 1H NMR Approach to Quantitative Tissue Oximetry Using Hexamethyldisiloxane," Magnetic Resonance in Medicine, 2006, 55:743-748.
Kodibagkar et al., "Proton Imaging of Siloxanes to Map Tissue Oxygenation Levels (PISTOL): A Tool for Quantitative Tissue Oximetry," NMR Biomed., 2008, 21(8):899-907.
Examination Report for EP 18714094.2, mailed Mar. 25, 2021 (6 pages).

* cited by examiner

10

16

26

10

14

16

26

28

6 mm

METHODS AND SYSTEMS FOR QUANTITATIVE MONITORING OF IN VIVO TUMOR OXYGENATION

REFERENCES TO RELATED APPLICATIONS

This application claims priority to U.S. Provisional Patent Application No. 62/466,615, filed Mar. 3, 2017, which is incorporated herein by reference.

BACKGROUND

A hallmark of solid tumors is the reduction in tissue oxygen content. The effect is attributed to a disrupted tumor vasculature and the greater demand for oxygen by the rapidly growing tumor. Tumor hypoxia has been linked to chemo- and radio-resistance, transition to more aggressive cell phenotypes, formation of metastasis, and generally a poor prognosis for the patient. The association between hypoxia and poor clinical outcome has been observed in a number of cancers including cervical, prostate, and head and neck carcinoma.

Attempts to overcome the poor prognosis and other adverse features of tumor hypoxia have focused on hypoxia targeting chemotherapeutics, efforts to induce re-oxygenation of the tumor, and delivery of an increased radiation dose to overcome hypoxia-induced resistance. The resistance to radiotherapy under hypoxic conditions is due to the ability of DNA, which is damaged during radiation therapy, to repair itself in the absence of oxygen. Prior radiobiological modeling results have shown that equivalent therapeutic outcomes can be achieved in hypoxic tumors with increased radiation doses when compared with lower doses in more well-oxygenated tumors.

While there has been a wealth of clinical data showing the negative impact of hypoxia, the techniques to overcome hypoxia have been of limited clinical utility due to a lack of an appropriate oxygen measurement technique. Much of the historical data regarding tumor hypoxia and its influence on radiotherapy was collected with the Eppendorf Oxygen Electrode (EOE), an electrochemical oxygen probe. The main benefit of the EOE was the ability to achieve absolute oxygen measurements. This probe, however, has since been discontinued. Wide clinical use of the EOE, while it was available, was limited because the probe needed to be re-inserted for each measurement. It was difficult to access tumors that were not near the surface of the body, and it is incompatible with MRI which is a preferred imaging modality for many cancer patients. The focus of in vivo oxygen sensing has since shifted to tracking endogenous markers and imaging based methods. One of the most well studied hypoxia markers is hypoxia inducible factor-1 (HIF-1α), a transcription factor that regulates cellular response to hypoxia and is often measured in serum or tissue by immunoassay. This marker is not always correlated with tumor oxygenation and may be upregulated due to non-hypoxia triggers. The most common imaging options include magnetic resonance imaging (MRI) and positron emission tomography (PET). The most well-known magnetic resonance-based method is tissue oxygen level dependent (TOLD) MRI, a tissue analog to the more well-known blood oxygen level dependent (BOLD) MRI. This method is not widely used clinically due to poor performance characteristics with physiologic motion and tissue-air interfaces. PET-based oxygen measurement options involve the use of 18F-fluoromisonidazole, a radioactive oxygen-sensitive tracer. PET has limited spatial resolution when mapping tumor oxygen content and co-registering with anatomical features. Repeated oxygen measurements with PET may also be confounded by the need to re-administer the radiotracer for each imaging session. This lack of resolution has been mitigated by combining PET data with MRI or computed tomography (CT), but results have not been sufficiently robust to enable clinical use.

High dose-rate interstitial brachytherapy (HDR-brachy), coupled with a viable oxygen measurement method, allows a physician to adjust the radiation dose distribution within a tumor based on the oxygen content in different tumor sub-volumes. HDR interstitial application is performed after external-beam radiation therapy, which is commonly delivered with sensitizing chemotherapy, to downsize the initial tumor volume and treat micrometastatic disease. HDR-brachy thereafter delivers a highly conformal boost dose to a localized region of residual tumor. Based on the physical properties of the Ir-192 brachytherapy source, there is rapid dose fall-off to adjacent normal tissue structures, such as the bladder, rectum and sigmoid. Typically, HDR interstitial brachytherapy for cervical involves the placement of 12-16 hollow cylindrical-cone-shaped tubes (catheters) within and around the tumor. The radio-isotope is programmed to travel into each individual catheter with variable source positions and time (typically seconds per position) with the use of a remote afterloader. The desired dose distribution is delivered over a 10-15 minute treatment. HDR interstitial brachytherapy treatment is most commonly delivered in the inpatient setting twice a day over 2-3 days for cervical cancer patients, although multiple outpatient treatments are also performed in select cases. Each brachytherapy treatment provides an opportunity to adjust the delivered dose to ensure maximum therapeutic outcome by optimizing tumor coverage with the prescription dose and limiting dose to the normal tissue structures and thereby reduce the risk of late radiation complication. Effectively overcoming tumor hypoxia with HDR-brachy should leverage quantitative oxygen measurements with spatial resolution, long-term spatial stability, and compatibility with the existing clinical practice.

MRI is emerging as the premier imaging modality for HDR-brachytherapy application and planning, due to its excellent soft tissue resolution for pelvic tumors and the surrounding normal tissues. Additionally, intra-operative procedure suites are available for rapidly and accurately placing catheters under MRI-guidance. Serial MRI imaging may be performed at multiple time points during the course of therapy to assess tumor response and to allow for modification of the radiation plan, known as adaptive planning.

It therefore would be desirable to provide an MRI-based method that permits accurate estimation of the hypoxic tumor regions during therapy. It also would be desirable to provide an MRI-based method, as well as devices and systems therefor, that can be integrated with the emerging image-guided brachytherapy practice in radiation oncology.

SUMMARY

In one aspect, methods are provided for monitoring in vivo tumor oxygenation in a patient. In some embodiments, the method includes (i) inserting at least one oxygen sensor unit, which comprises a catheter and a first quantity of a solid-state contrast agent for oxygen, into a first selected subvolume of a tumor located within the patient; (ii) using magnetic resonance (MR) to assess an MR property of the at least one oxygen sensor unit; and (iii) quantifying the oxygen level in the first selected subvolume of the tumor, based on the assessed MR property and a calibration curve.

The method may further include inserting a second oxygen sensor unit into a second selected subvolume of the tumor, the first and second subvolumes being different volumes from one another, wherein the second oxygen sensor unit comprises a second quantity of the solid-state contrast agent for oxygen. In some embodiments, a total of from four to twenty of the oxygen sensor units are inserted into the tumor and surrounding tissues. The MR property may be the MR relaxation time ($T_1$) of protons in the at least one oxygen sensor unit, and the MR property may be acquired using magnetic resonance imaging (MRI).

In a particular embodiment of the methods, magnetic resonance imaging is used to assess the MR relaxation time ($T_1$) of protons in the at least one oxygen sensor unit; the quantifying of the oxygen level in the first selected subvolume of the tumor is based on the assessed MR relaxation time and a calibration curve; and the quantified oxygen level in the first selected subvolume of the tumor is used to select or adjust delivery of a high dose rate brachytherapy to the tumor.

In another embodiment, the method for monitoring in vivo tumor oxygenation in a patient includes: (i) inserting at least one oxygen sensor unit, which comprises a catheter and a first quantity of a solid-state contrast agent for oxygen, into a first selected subvolume of a tumor located within the patient; (ii) using MR to assess the MR relaxation time of protons in the at least one oxygen sensor unit; (iii) determining a quantitative reference point for a qualitative oxygen evaluation method; and (iv) determining, based at least in part on the quantitative reference point, quantitative oxygen levels in one or more subvolumes of the tumor measured with the qualitative oxygen evaluation method. In various embodiments, the qualitative oxygen evaluation method may be based on blood oxygen dependent MRI, tissue oxygen dependent MRI, or positron emmission tomography.

In another aspect, improved methods are provided for treating a solid tumor in a patient by using the measured tumor oxygenation. In some embodiments, the methods include (i) selectively placing a plurality of oxygen sensor units, comprising a catheter and a solid-state contrast agent for oxygen, directly into the tumor and/or surrounding tissues; (ii) selectively placing a plurality of radiation source catheters directly into the tumor and/or surrounding tissues to deliver high dose rate brachytherapy; and (iii) measuring oxygen levels about the solid-state contrast agent for oxygen, using MRI to assess the MR relaxation time ($T_1$) of protons in the solid-state contrast agent for oxygen, wherein said measuring is conducted before, during, and/or after the high dose rate brachytherapy.

For example, the dose of the high dose rate brachytherapy may be adjusted based on a measured hypoxia of a tumor sub-volume. The adjustment may include altering the relative position and/or time of a radiation source within one or more of the plurality of radiation source catheters, in order to increase the radiation dose in the tumor sub-volume in which hypoxia is measured.

In another aspect, medical devices are provided for monitoring in vivo tissue oxygenation. In some embodiments, the device includes a catheter having at least a distal end portion configured for insertion into tissue within a patient; and one or more units of a solid-state contrast agent for oxygen sensing, wherein the catheter comprises (i) an oxygen-permeable annular tube in which the one or more units of a solid-state contrast agent for oxygen sensing are disposed, (ii) an annular tube in which a portion is oxygen permeable in which the one or more units of a solid-state contrast agent for oxygen sensing are disposed, (iii) an outer surface onto which the one or more units of a solid-state contrast agent for oxygen sensing are fixed, or (iv) a combination of (i), (ii), and (iii). The solid-state contrast agent for oxygen may include a first silicone composition and a second silicone composition, wherein the first and second silicone compositions are different from one another. For example, the solid-state contrast agent for oxygen sensing may comprise a liquid phase silicone dispersed or otherwise mechanically entrapped in a chemically cross-linked silicone elastomer matrix.

In some embodiments, the catheter comprises an annular tube having a lumen terminating at a closed distal end, and the solid-state contrast agent for oxygen is disposed in the lumen in region about the distal end. The annular tube may include a sidewall having one or more apertures located to permit oxygen to diffuse therethrough and contact the solid-state contrast agent. The annular tube may include an internal channel configured to receive a radiation source and/or to accept a coil for making a MR measurement.

BRIEF DESCRIPTION OF THE DRAWINGS

Referring now to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

DETAILED DESCRIPTION

Figure 1:
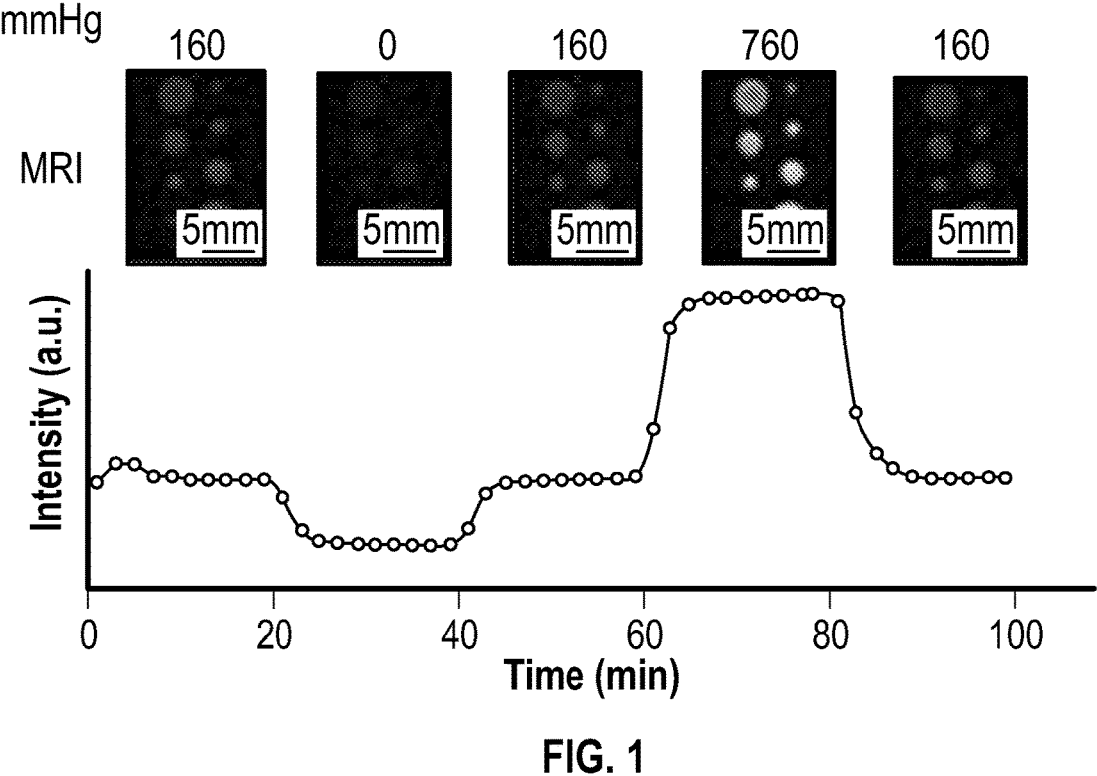
FIG. 1 depicts an oxygen sensor's response to tissue oxygen content, as assessed using MRI in accordance with one embodiment of the present disclosure.

A new class of oxygen sensors are provided for measuring oxygen levels with magnetic resonance measuring, including magnetic resonance imaging (MRI), that are well-suited for medical applications. The oxygen sensors generally include one or more units of a solid-state contrast agent (SSCA) for oxygen that is measurable with MRI. The term "solid-state" as used herein with reference to a solid-state contrast agent refers to a material or combination of materials that has at least a solid phase that retains its structure without support.

The oxygen sensors are capable of distinguishing between different concentrations of dissolved oxygen in a surrounding environment, such as a patient's tissue, and responding to changes in environmental oxygenation conditions, such as decreases or increases in oxygen levels of the surrounding environment. Oxygen quantification can be achieved by measuring the MRI relaxation time (for example, $T_1$) of protons in the oxygen sensor, particularly protons in the solid-state contrast agent. Multiexponential fitting may be used to separate different components of the solid-state contrast agent or a component of interest be isolated during data collection by adjusting the settings of the MRI. $T_1$ represents the time duration in which the protons return to their equilibrium quantum state following excitation to a higher energy level during an MRI scan. In embodiments, the oxygen sensor and methods of using the same may utilize the direct measurement of the NMR relaxivity of a sensing medium in contact with dissolved oxygen.

The solid-state contrast agent may be silicone-based, such that the solid-state contrast agent is completely passive and measureable using MRI. Silicone can limit the ingress of biological material into the contrast agent because of the hydrophobic nature of silicone, and this can ensure accurate oxygen measurements are made as well as protect the oxygen sensors from contamination. The relaxation time of silicone is influenced by the concentration of oxygen present in the material in a manner similar to how a traditional gadolinium (Gd) contrast agent, used commonly with MRI, modifies the tissue relaxation time. Molecular oxygen and Gd contrast agents are both paramagnetic. The paramagnetic nature of these materials serves as a relaxation sink and speeds the relaxation process as their concentration increases. The measured relaxation times can be converted to an oxygen partial pressure based on a predetermined, application independent, calibration curve.

A silicone-based solid-state contrast agent may have a chemically cross-linked polymer matrix that allows it to be formed into many different shapes or integrated with other medical equipment. The silicone-based solid-state contrast agent may be placed within a tissue, and the cross-linked property can enable the solid-state contrast agent to remain at the site of placement, thereby allowing for repeated oxygen measurements at the same tissue location. Repeated sampling in the same location can be important when tracking tumor hypoxia progression because of the temporal and spatial variability associated with tumor hypoxia.

An oxygen sensor and solid-state contrast agent can have high oxygen solubility and permeability, which allow the oxygen sensor and solid-state contrast agent to respond rapidly to fluctuations in tissue oxygen content. In embodiments, an oxygen sensor and solid-state contrast agent can re-equilibrate when the oxygen content is changed from 0 mmHg (0% O2) to 160 mmHg (21% O2) in under 10 minutes, and this rapid response can be used to measure acute hypoxia within a tumor.

An oxygen sensor, or a portion thereof, can be deployable adjacent to a tissue site of a patient or inside a tissue site of a patient. The term "patient" generally refers to a human, although other mammals may be considered a patient in some applications. An oxygen sensor, or a portion thereof, can be implantable within a patient. The terms "deployable" and "implantable" as used herein refer to a device that is configured for deployment and implantation, respectively. The deployment may be temporary, for example on on the order of a few minutes or hours. A partially implanted oxygen sensor means that a first portion of the oxygen sensor device extends out of the patient transcutaneously or from an anatomical orifice and a second portion of the oxygen sensor device does not extend out of the patient transcutaneously or from an anatomical orifice. A wholly implanted oxygen sensor means that there is not a portion of the oxygen sensor device that extends out of the patient transcutaneously or from an anatomical orifice.

An oxygen sensor may be made in various shapes and sizes, and can be designed in shapes that facilitate implantation. An oxygen sensor may be used in the treatment of cancers of the cervix, prostate, breast, skin, brain, eye, head and neck region (e.g., lip, floor of mouth, tongue, nasopharynx and oropharynx), respiratory tract (e.g., trachea and bronchi), digestive tract (e.g., esophagus, gall bladder, bile-ducts, rectum, anus), urinary tract (e.g., bladder, urethra, penis), female reproductive tract (e.g. uterus, vagina, vulva), and soft tissues, and may be sized and shaped for deployment and/or implantation at any of these tissue sites.

An oxygen sensor can be exposed to or introduced into a subject's body by a surgical or medical procedure, and can remain there after the procedure (e.g., a permanent implant). For example, an oxygen sensor can be sized and shaped to be deployed or implanted in the body of a human or animal and to remain deployed or implanted for a period of time, such as 2 days or more. The oxygen sensor generally has suitable sterility, biocompatibility, and physical and/or chemical integrity to be deployed or implanted and remain deployed or implanted over the intended duration of use of the oxygen sensor.

An oxygen sensor may include or be a biocompatible elongate device, such as a catheter or needle, having one or more units of solid-state contrast agent operably associated therewith, e.g., directly attached or disposed within. The solid-state contrast agent may be or include a sensing material that is a magnetic resonance contrast agent for oxygen, and the oxygen sensor can be configured to indicate the dissolved oxygen concentration of the surrounding tissue or environment when subjected to magnetic resonance based methods. The solid-state contrast agent can be disposed on an outer surface of the elongate device, in an interior of the elongate device when a portion of the outer surface is oxygen permeable, contains a path for oxygen diffusion, or a combination thereof.

Methods for monitoring tissue oxygenation, in vivo or ex vivo, in a patient using an oxygen sensor, are also provided herein. The methods for monitoring tissue oxygenation can include deploying an oxygen sensor at a tissue site of a patient, and thereafter subjecting the tissue site to electromagnetic radiation and employing magnetic resonance-based methods to analyze the dissolved oxygen concentration of the tissue. That is, the methods can measure the dissolved oxygen concentration of a patient's tissue. An oxygen sensor can be subjected to repeated measurements. An oxygen sensor can be deployed or implanted at a specific target tissue site of interest to allow for site-specific measurement and analysis. An oxygen sensor may be employed in various types patients or subjects including human or other mammals.

Methods for treating a tumor in a patient are also provided. The methods for treatment can include deploying an oxygen sensor at a tissue site of a patient that has a tumor, measuring an oxygen concentration of the tissue site by magnetic resonance based methods, and performing radiation therapy (e.g. external beam or brachytherapy) to treat the tumor based at least in part on the measured oxygen concentration. The methods for treatment may include tailoring the brachytherapy to a patient's needs based on the measured oxygen concentrations at the tissue site. For example, tumor sub-volumes determined to be hypoxic may require radiation dose escalation for effective therapy, and a clinician may adjust the placement of treatment catheters, which are devices that temporarily contain radiation sources, at the tissue site such that more treatment catheters are proximate to the tumor and/or selectively increase radiation doses delivered by specific treatment catheters proximate to hypoxic regions of the tumor.

Oxygen Sensors

Oxygen sensors are provided for measuring oxygen levels of a tissue in vivo or ex vivo. An oxygen sensor, or a portion thereof, can be deployable adjacent to a tissue site of a patient or inside a tissue site of a patient. An oxygen sensor, or a portion thereof, can be implantable within a patient. An oxygen sensor can be used to take repeated measurements of dissolved oxygen levels at the tissue site.

An oxygen sensor can be configured to be utilized with standard magnetic resonance-based spectroscopy. As used herein, the terms "magnetic resonance-based spectroscopy" and "magnetic resonance-based methods" broadly refer to analytical and measurement techniques in which a material, such as a material present at a tissue site, is subjected to electromagnetic radiation for purposes of characterization. In particular, the term encompasses analytical techniques in which a magnetic field is applied to a material and the effect of the applied magnetic field on the material is measured or observed, and includes techniques such as H1 NMR (hydrogen-1 nuclear magnetic resonance) and MRI (magnetic resonance imaging). Although not limited to H1 NMR based techniques, this is a convenient approach because of the ready access to equipment, appropriate pulse sequences, and software.

An oxygen sensor can include a biocompatible elongate device having one or more units of solid-state contrast agent associated therewith. As used herein, the term "elongate device" refers to essentially any narrow, elongated structure capable of positioning a solid-state contrast agent in a desired and operable location in vivo or ex vivo, and includes elongate tubular devices and elongate solid devices.

In embodiments, an oxygen sensor includes an elongate tubular device with a lumen, such as a catheter or needle, having one or more units of solid-state contrast agent operably associated therewith. An elongate tubular device can be open or closed at the end inserted into the tissue. The lumen may extend along the length of the tubular device and operate as a channel. The lumen may be dimensioned to accept a radiation source used in brachytherapy and/or a radiofrequency coil (RF coil) such as a transmit, receive, or transmit-receive coil. An elongate tubular device can be an oxygen-permeable silicone closed-end catheter suitable for human use.

In embodiments, an oxygen sensor includes an elongate solid device with no lumen, such as a solid rod, having one or more units of solid-state contrast agent operably associated therewith.

In embodiments, an elongate device is made of a rigid material. In a preferred embodiment, the elongate device is made of a material such as a biocompatible polymer (e.g., ABS) or a composite. Examples of suitable materials that an elongate device may be made from include silicone, silicone rubber, nylon, polyurethane, polyethylene terephthalate (PET), latex, polyimides, thermoplastic elastomers, polyether ether ketone (PEEK), or carbon fiber. Non-ferrous metals may form part of the device in some embodiments. An elongate device may be made of materials that are intended to degrade over a given duration or not degrade and either be left in tissue or removed from the tissue at the end of a given measurement or set of measurements.

In embodiments, an elongate device is constructed of a biocompatible material that has high oxygen permeability. This allows the inside of an elongate device, which can have a solid-state contrast agent disposed therein, to equilibrate quickly with the surrounding tissue in which it is placed. In embodiments, an elongate device is constructed of silicone and thus has high oxygen permeability.

In embodiments, an elongate device is constructed of a biocompatible material that has low or no oxygen permeability. In these embodiments, the elongate device may include one or more apertures therein providing a passage for oxygen to diffuse and contact a solid-state contrast agent disposed within the elongate device. For example, an elongate device with low oxygen permeability may be modified by drilling, cutting, and/or machining through-holes to improve oxygen permeability and exchange into the elongate device.

In embodiments, an elongate device is constructed of a solid-state contrast agent. For example, a solid-state contrast agent may be made from a medical grade material that is suitable for placement in direct contact with tissue, so it may not be necessary to seal the solid-state contrast agent in a medically approved device such as a catheter or needle.

An elongate device can have one or more apertures or indentations therein. The apertures/indentations may be introduced by, for example, forming, drilling, cutting, and/or machining holes into the elongate device. Apertures may be pre-existing in off-the-shelf elongate devices. For example, commercial catheters may contain small holes near the distal end.

The apertures/indentations can operate as reservoirs or depots for receiving solid-state contrast agent. The apertures can allow deposition of a solid-state contrast agent into an inner lumen of an elongate device. The apertures can provide a passage for oxygen to diffuse through an exterior surface of the elongate device, which may have low or no oxygen permeability, and into an interior of the elongate device, which may contain a solid-state contrast agent. In embodiments, an elongate device may have one or more depots for receiving a solid-state contrast agent on its external surface.

In embodiments, the apertures/indentations are partially or wholly filled with a solid-state contrast agent. In embodiments, the apertures/indentations are partially or wholly filled, or otherwise sealed, with an oxygen permeable material suitable for medical use, such as a silicone epoxy, silicone adhesive, or a supporting material such as PDMS, to allow oxygen diffusion into an interior of the elongate device while also preventing contact between a patient's tissue and a solid-state contrast agent contained in the elongate device's interior. In embodiments, the apertures are not filled with a solid-state material and are hollow. In these embodiments, the apertures may allow ingress of a fluidic biological medium and/or oxygen.

An oxygen sensor or elongate device can have a diameter or width that is appropriate for a particular tissue site. In embodiments, the oxygen sensor or elongate device has a diameter of from about 2.5 mm to about 3 mm, e.g. about 2.7 mm. In embodiments, the oxygen sensor or elongate device has a diameter of from about 1.5 mm to about 2.5 mm, e.g. about 2 mm. In embodiments, the oxygen sensor or elongate device has a diameter of from about 0.8 mm to about 1.2 mm, e.g. about 1 mm.

An oxygen sensor can include one or more units of solid-state contrast agent. A solid-state contrast agent can be a polymeric article that is suited for sensing oxygen. A solid-state contrast agent may be or include a sensing material that is a magnetic resonance contrast agent for oxygen. The term "magnetic resonance contrast agent for oxygen" as used herein refers to a material suitable for indicating the dissolved oxygen concentration within the material when employing magnetic resonance-based spectroscopy by enhancing the desired signal beyond that which is provided by background molecules (i.e., molecules naturally present at the site of implantation), such as water molecules. For example, a magnetic resonance contrast agent for oxygen may have a spin-lattice relaxation time ($T_1$) that is dependent on dissolved oxygen concentration. In embodiments, a solid-state contrast agent can exhibit sufficient sensitivity to resolve oxygen concentration at low oxygen concentrations, particularly between about 0% and 2% oxygen.

Proton spins can be flipped into different planes and axis of rotation when protons are irradiated with a radio frequency (RF) pulse. This change in rotation is temporary and the direction in magnetic moment eventually returns to the equilibrium state. In particular, the restoration of magnetic moments to the original axis can be characterized by $T_1$. As intrinsic $T_1$ is a material property, it can provide a reliable source of contrast in MRI images. (Intrinsic T1 is a property of the material, but that T1 can be altered by other species like gadolinium contrast agents or oxygen (as is the case here)). $T_1$ maps are frequently used in imaging applications to distinguish between different anatomical structures. Paramagnetic molecules or particulates that decrease the relaxation time of surrounding molecules can be used to enhance contrast of $T_1$ maps. They can also provide a mechanism for sensing. For example, dissolved oxygen molecules are paramagnetic and can decrease the $T_1$ relaxation time of water protons (or other spin bearing atoms) surrounding it. Thus, the $T_1$ value can depend on the concentration of dissolved oxygen and thus dissolved oxygen concentration can be determined by measuring the relaxation time of the sensor.

The relaxation time of the sensor can measured by measuring the sensor as a single voxel or as multiple voxels. A region of interest can be defined to determine which voxels (if there are multiple) to include in the fitting to obtain the relaxation time of the sensor for obtaining an oxygen measurement. The voxels can be averaged before fitting to obtain the relaxation time or after the fitting has been done on a per voxel basis.

The measurement of the relaxation time may be obtained using a pulse sequence and data acquisition parameters suitable for making a quantitative $T_1$ measurements such as a saturation recovery or inversion recovery pulse sequence. A single $T_1$ measurement may include acquisition of multiple inversions to provide sufficient data to fit to the equation and extract a $T_1$ value. Parameters for the inversion recovery pulse sequence may include an echo time of 15 ms, a repetition time of 3000 ms, and slice thickness of 2 mm. Measurement of the solid-state contrast agent or sensor may include the use of one or more receive coils including the spine coil, body matrix coil, endorectal coil or a coil incorporated within the sensor. Multiple slices or averages slices may be collected. Multiple slices may be collected to determine sensor positioning and then a single slice measured for data acquisition.

A sensing material can be or include liquid or solid compounds having magnetic resonance properties that are sensitive to oxygen concentration. Particulate suspensions or emulsions of sensing materials are contemplated. A sensing material can be biocompatible.

Silicones, also known as polysiloxanes, such as those formed from low molecular weight siloxanes, may be particularly useful in oxygen sensors as a sensing material (e.g. as a magnetic resonance contrast agent for oxygen). Low molecular weight siloxanes can be read using MR-based spectroscopy (e.g., H1 NMR or MRI), and are more sensitive to concentrations of dissolved oxygen than water protons. An advantage of using low molecular weight siloxanes as a sensing material is that they can give a different magnetic resonance signature than water and can be easily distinguished from background water molecules inside the body. One particularly useful siloxane is hexamethyldisiloxane, which is a highly hydrophobic and non-polar molecule. This molecule has a high solubility for oxygen, and has a single peak for hydrogen NMR. Other useful siloxanes include octamethyltrisiloxane, decamethyltetrasiloxane, dodecamethylpentasiloxane, hexamethylcyclotrisiloxane, octamethylcyclotetrasilane, decamethylgclopentasiloxane, and dodecamethylcyclohexasiloxane.

A solid-state contrast agent may include a supporting material. A supporting material can provide structure and rigidity to the solid-state contrast agent so that the solid-state agent maintains its shape. A supporting material may entrap, encapsulate, or otherwise contain therein a sensing material, such as a liquid siloxane. A supporting material can be permeable to oxygen and allow the diffusion of oxygen therethrough. A supporting material may form an outer membrane of a solid-state contrast agent that is impermeable to a sensing material, thereby preventing a sensing material from escaping from the solid-state contrast agent. A supporting material can be biocompatible. A supporting material may be a polymeric matrix material permeable to oxygen and configured to prevent the diffusion of a sensing material for oxygen from the solid-state contrast agent at least over the period the oxygen sensor is deployed in vivo or ex vivo, e.g. 1 to 6 months. An exemplary supporting material is a polymeric matrix material made of polydimethylsiloxane ("PDMS"). Other suitable supporting materials include polymeric matrix materials made from various UV-curable epoxies and silicones.

A solid-state contrast agent may consist of only solid-phase materials, and therefore be an entirely solid-phase article. In embodiments, a solid-state contrast agent is a solid-state, solid, polymeric article that has sensing material for oxygen integrated within the polymeric structure of the article, e.g., by the direct incorporation of magnetic resonance-readable, oxygen sensitive material into the polymeric matrix. In embodiments, a solid-state contrast agent may be a cured composite polymeric article comprising a solid-state sensing material for oxygen dispersed inside or throughout a solid-state supporting material such as a polymeric matrix.

An oxygen sensor containing solid-state contrast agent may be used to provide a quantitative reference point for a qualitative oxygen map such as BOLD, TOLD, or PET/CT. Quantitative oxygen values for other portions of the tumor may then be determined by extrapolating the relative quantitative values from a common point. To improve the accuracy of the mapping, multiple oxygen sensors may be used.

A solid-state contrast agent may be a hybrid article comprising both solid-phase materials and liquid-phase materials. For example, a solid-state contrast agent may include a solid-phase supporting material that confers structural rigidity and entraps or otherwise contains therein a liquid-phase sensing material. In embodiments, a solid-state contrast agent may be a cured article comprising a liquid-phase sensing material for oxygen dispersed throughout a solid-phase supporting material such as a cross-linked polymeric matrix. For example, a solid-state contrast agent may comprise a polydimethylsiloxane supporting matrix and a liquid siloxane, such as dodecamethylpentasiloxane or hexamethyldisiloxane, dispersed throughout the polymeric supporting matrix. In some embodiments, a solid-state contrast agent may have a shell that has a primary purpose of providing mechanical stability and permeability to oxygen and an interior volume in which the sensing material resides. The shell and interior volume materials may be very similar to one another in their chemistry, but they may differ in their mechanical properties. The interior may be, for example, a low molecular weight or liquid silicone derived material but the shell may be a high molecular weight or cross-linked silicone material in such a way that it provides sufficient strength.

In one embodiment, a solid-state contrast agent combines a liquid phase silicone and a chemically cross-linked silicone elastomer matrix. In this embodiment, the matrix serves to mechanically entrap the more sensitive liquid silicone. The solid/liquid combination prevents diffusion of the sensing material, and a single deployment of contrast agent can be repeatedly measured.

In embodiments, a solid-state contrast agent may be fabricated by adding a sensing material for oxygen, such as a lower molecular weight siloxane, to an uncured liquid polymer base, such as SYLGARD® 184 elastomer base from Dow Coming, and mixing thoroughly. An appropriate curing agent may then may be added, and the mixture/ solution may be cured, e.g., with heat treatment, to form a solid-state contrast agent. Fabricated solid-state contrast agents may be directly used in oxygen sensing applications without further modification or they can be coated with other materials to enhance biocompatibility, stability, and/or containment of the sensing material for oxygen.

One or more units of solid-state contrast agent may be disposed and/or secured on, in, or both, an elongate device in one more positions. A solid-state contrast agent may be disposed or secured inside an elongate device in one or more positions. A solid-state contrast agent may be disposed or secured onto one or more outer portions of an elongate device, in which case the elongate device need not be oxygen permeable. In embodiments, a solid-state contrast agent may be continuous along the length of an elongate device or along a portion of the elongate device.

A solid-state contrast agent can be incorporated into an elongate device, e.g., catheter, any number of ways. In embodiments, a solid-state contrast agent can be disposed in an aperture, indentation, lumen, and/or reservoir of an elongate device and contained therein by sealing, plugging, and/or covering an opening to the aperture, indentation, lumen, and/or reservoir with, for example, a layer of silicone epoxy, silicone adhesive, or a supporting material such as PDMS. In embodiments, a solid-state contrast agent can be disposed in an aperture, indentation, lumen, and/or reservoir of an elongate device and held in place by an interference friction fit or an adhesive. In embodiments, a solid-state contrast agent can be disposed in an aperture, indentation, lumen, and/or reservoir of an elongate device and held in place by polymerizing or cross-linking the solid-state contrast agent to the elongate device. In some embodiments, unsolidified (e.g. liquid) solid-state contrast agent precursor chemicals can be disposed in an aperture, indentation, lumen, and/or reservoir of an elongate device, and then polymerized by introducing a curing agent and/or allowing a certain amount of time to elapse. The resulting polymerized solid-state contrast agent may be geometrically restrained within the elongate device because the geometry/dimensions of the solid-state contrast agent prevent it from passing through any apertures in the elongate device or otherwise separating from the elongate device. In some embodiments, a solid-state contrast agent forms an elongate device. That is, in some embodiments, a solid-state contrast agent is an elongate device.

One or more units of solid-state contrast agent may be disposed partially or wholly along the length of an elongate device. Each unit of solid-state contrast agent may extend, for example, about 1 mm along the length of an elongate device, and each unit of solid-state contrast agent may be spaced apart from other solid-state contrast agent by a minimum distance, for example, a distance of about 1 mm.

In some embodiments, an oxygen sensor is designed for in vivo or ex vivo placement and a solid-state contrast agent is placed inside a biocompatible elongate tubular device, such as a catheter or needle, to keep the solid-state contrast agent from contacting surrounding tissue. This configuration can ensure that only medically approved materials come in contact with a patient's tissue.

In some embodiments, an oxygen sensor and/or an elongate device may be configured to accept a radiation source and/or a RF coil such as a transmit, receive, or a transmit-receive coil. This may be achieved by employing an elongate device that has a channel for radiation source and/or RF coil insertion, such as an elongate tubular device like a catheter or needle. In some embodiments, an elongate device may have a radiation source disposed therein. In some embodiments, an elongate device may have a RF coil disposed therein. A RF coil may be incorporated in an oxygen sensor to speed measurements or improve locating the oxygen sensor in vivo. An RF coil may be temporarily or permanently incorporated into the oxygen sensor.

Figure 4A:
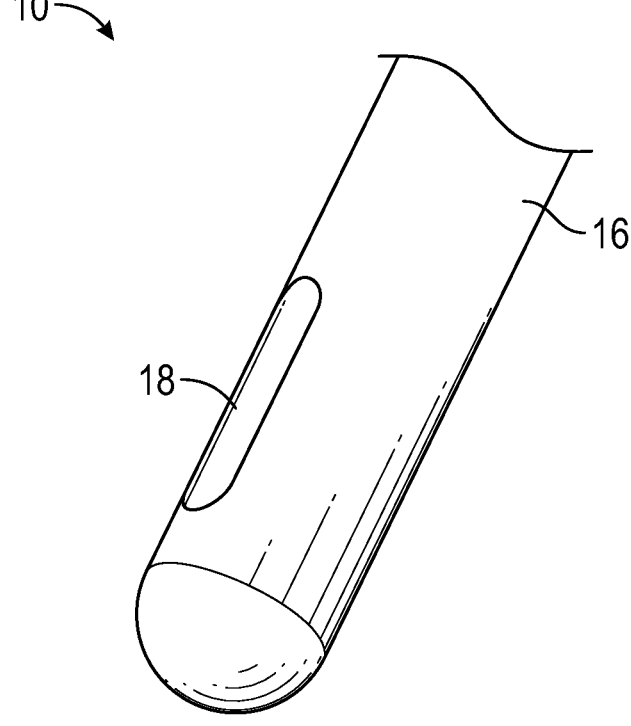
FIG. 4A is a perspective view of an oxygen sensor in accordance with one embodiment of the present disclosure.
Figure 4B:
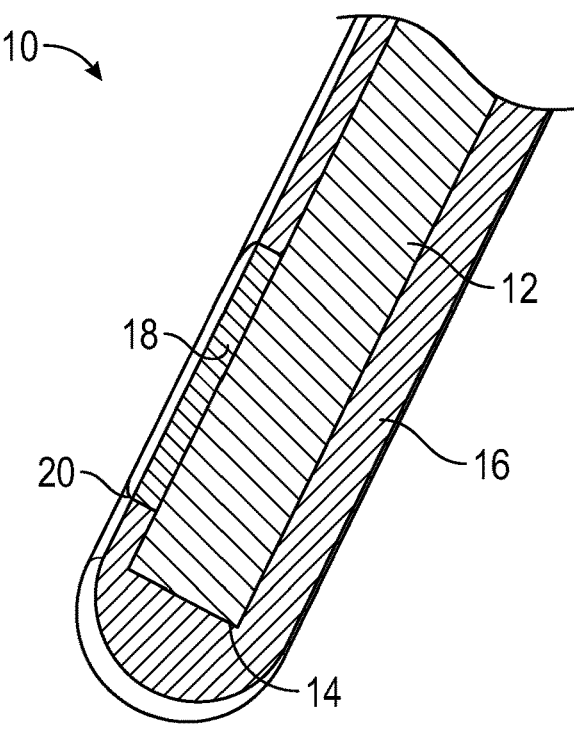
FIG. 4B is a cross-sectional view of the oxygen sensor shown in FIG. 4A.

FIGS. 4A-4B show the distal end portion of one embodiment of an oxygen sensor 10, in which FIG. 4A shows a perspective view of oxygen sensor 10 and FIG. 4B shows a cross-sectional view of oxygen sensor 10. In this embodiment, solid-state contrast agent 12 is located inside the lumen 14 of an oxygen permeable elongate device 16. The oxygen permeable elongate device 16 is a catheter made of silicone, although other biocompatible and oxygen permeable polymeric materials may be used. In the illustrated embodiment, a silicone adhesive 18 is used to close off a pre-formed opening 20 in the catheter. In other embodiments, the distal end portion of the catheter has no pre-formed opening in need of closing, and no silicone adhesive is needed.

Figure 5A:
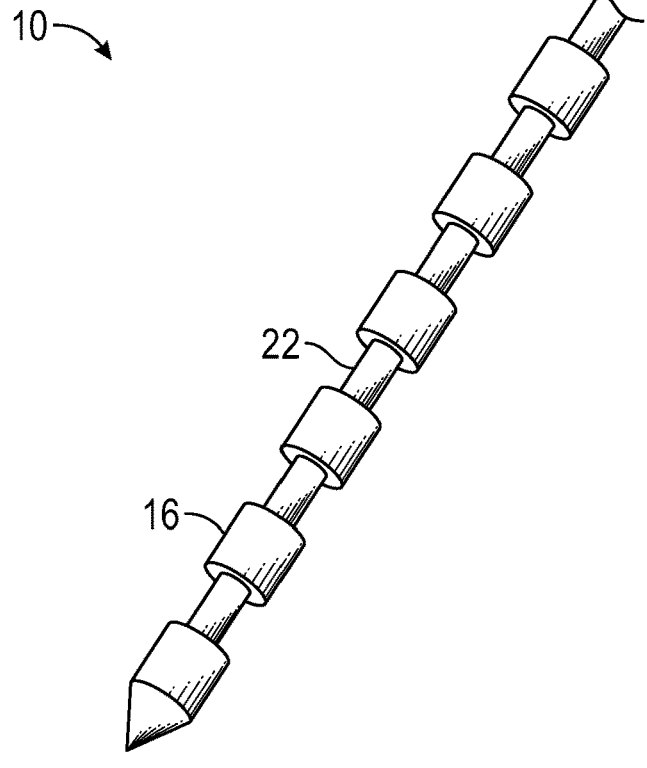
FIG. 5A is a perspective view of an oxygen sensor without its solid-state contrast agent in accordance with one embodiment of the present disclosure.
Figure 5B:
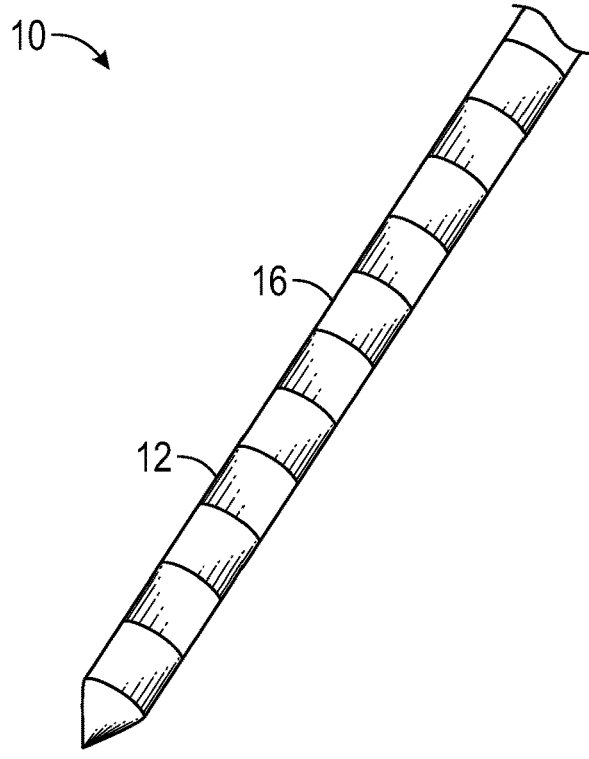
FIG. 5B is a perspective view of the oxygen sensor shown in FIG. 5A with its solid-state contrast agent in accordance with one embodiment of the present disclosure.
Figure 5C:
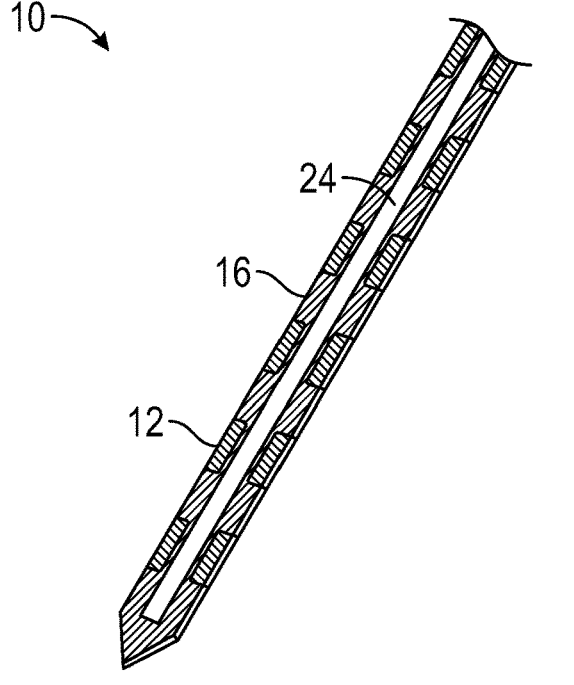
FIG. 5C is a cross-sectional view of the oxygen sensor shown in FIGS. 5A-5B.

FIGS. 5A-5C show the distal end portion of another embodiment of an oxygen sensor 10, in which FIG. 5A shows a perspective view of an oxygen sensor 10 with solid-state contrast agent 12 removed, FIG. 5B shows a perspective view of an oxygen sensor 10 with solid-state contrast agent 12 left in the sensor, and FIG. 5C shows a cross-sectional view of oxygen sensor 10. In this embodiment, an elongate device 16 includes a series of annular shaped indentations 22 in which units of solid-state contrast agent 12 are secured. The indentations 22 are spaced along the length of the elongate device 16. In this embodiment, each indentation 22 has a length of about 1 mm, and the space between adjacent units of the solid-state contrast agent 12 is also about 1 mm. In this embodiment, the units of contrast agent 12 are annular shaped and fill the indentations 22, such that the outer sidewall surface of the oxygen sensor 10 is substantially smooth and cylindrical in shape.

In this embodiment, the same elongate device 16 that incorporates the solid-state contrast agent 12 may also accept a radiation source. This may be achieved by having a channel 24 for radiation source insertion in elongate device 16, such as those found in an elongate tubular device like a catheter or needle. The channel 24, in addition to permitting radiation source insertion, may be used for receiving a stylet that increases the rigidity of the elongate device 16 during the insertion process. Such a stylet may be made of metal, such as tungsten, for example. A transmit, receive, or a transmit-receive coil may also be inserted in channel 24 of elongate device 16 and left in place or removed before the radiation source is added. If the elongate device 16 is made of an oxygen permeable material, then one or more units of solid-state contrast agent 12 may be inserted in channel 24 of elongate device 16. The solid-state contrast agent 12 in channel 24 may be removed before the radiation source is inserted.

Figure 6A:
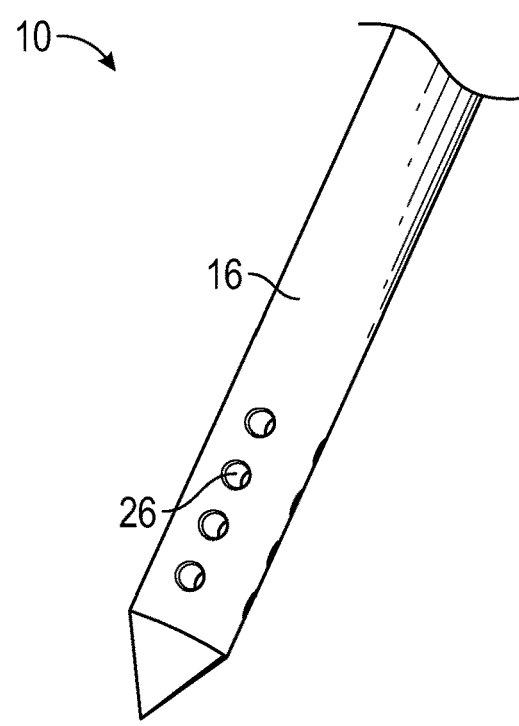
FIG. 6A is a perspective view of an oxygen sensor without its solid-state contrast agent in accordance with another embodiment of the present disclosure.
Figure 6B:
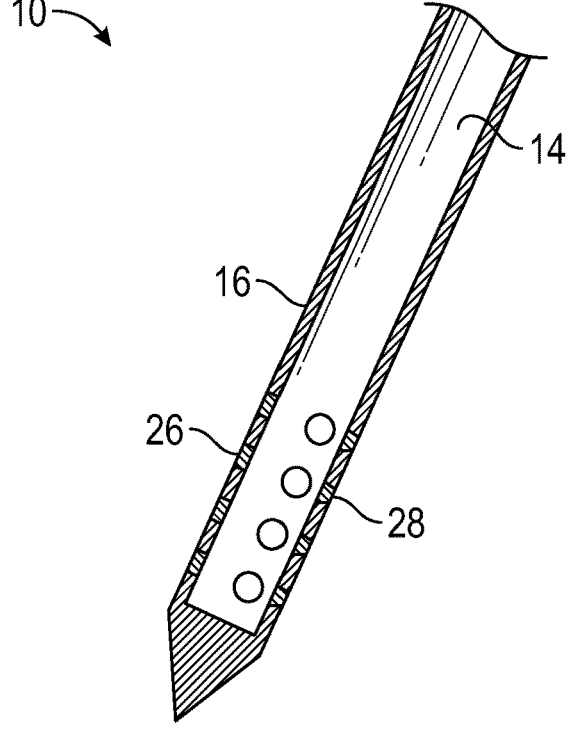
FIG. 6B is a cross-sectional view of the oxygen sensor shown in FIG. 6A with its solid-state contrast agent in accordance with another embodiment of the present disclosure.

FIGS. 6A-6B show the distal end portion of another embodiment of an oxygen sensor 10, in which FIG. 6A shows a perspective view of an oxygen sensor 10 having an elongate device 16 with solid-state contrast agent 12 removed and holes 26 to be filled and FIG. 6B shows a cross-sectional view of an oxygen sensor 10 having an elongate device 16 with holes 26 that are filled. In this embodiment, a rigid elongate device 16 such as a hollow catheter has holes 26 formed into the sides of the elongate device 16. The holes 26 can allow oxygen diffusion from outside of the elongate device 16 to the inside of the elongate device 16. The holes 26 may be filled with an oxygen permeable material 28 such as silicone. The holes 26 may be filled with a solid-state contrast agent. The lumen 14 may be empty. Alternatively, the lumen 14 may contain solid-state contrast agent.

Figure 7A:
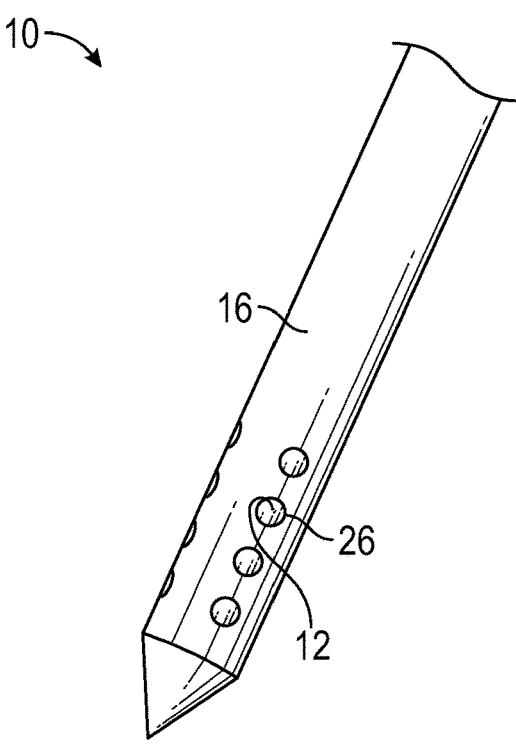
FIG. 7A is a perspective view of an oxygen sensor in accordance with another embodiment of the present disclosure.
Figure 7B:
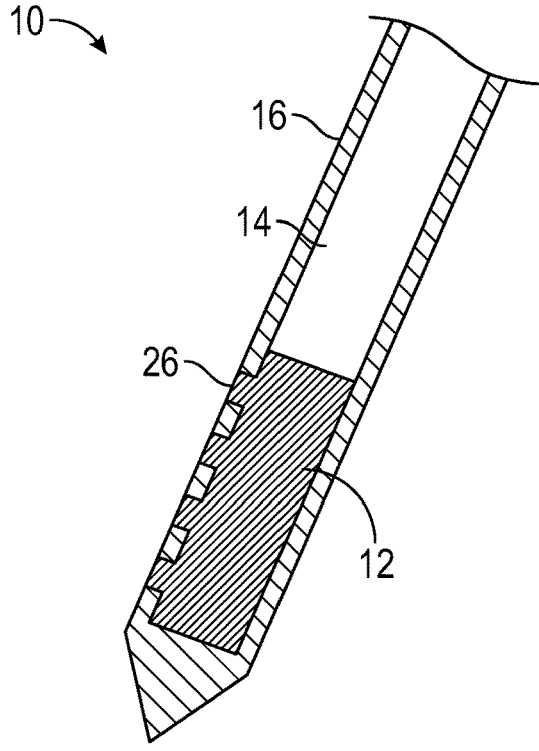
FIG. 7B is a cross-sectional view of the oxygen sensor shown in FIG. 7A in accordance with another embodiment of the present disclosure.

FIGS. 7A-7B show the distal end portion of another embodiment of an oxygen sensor 10, in which FIG. 7A shows a perspective view of oxygen sensor 10 and FIG. 7B shows a cross-sectional view of oxygen sensor 10. In this embodiment, a rigid hollow elongate device 16 has holes 26 formed into its side to allow oxygen diffusion from outside of the elongate device 16 to the inside of the elongate device 16. The elongate device 16 has a lumen 14 (e.g., a channel) in the space adjacent the holes 26. The holes 26, lumen 14, or both may be filled with solid-state contrast agent 12. The holes 26 and lumen 14 may be filled so that a continuous piece of material forms. Holes 26 may be filled with a silicone that is not solid-state contrast agent 12. Solid-state contrast agent 12 may fill at least a portion of lumen 14.

Figure 11A:
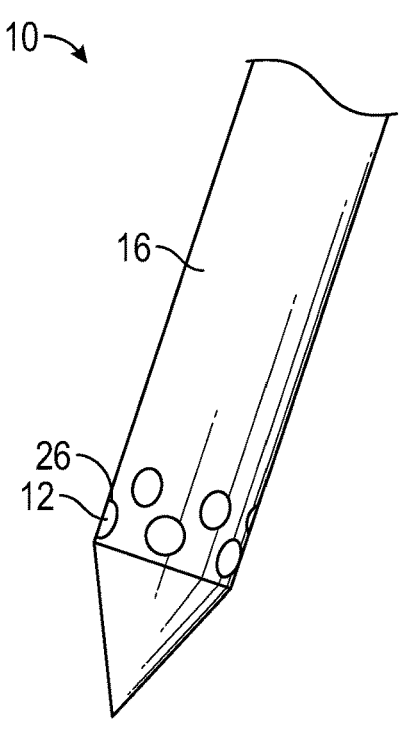
FIG. 11A is a perspective view of an oxygen sensor in accordance with another embodiment of the present disclosure.
Figure 11B:
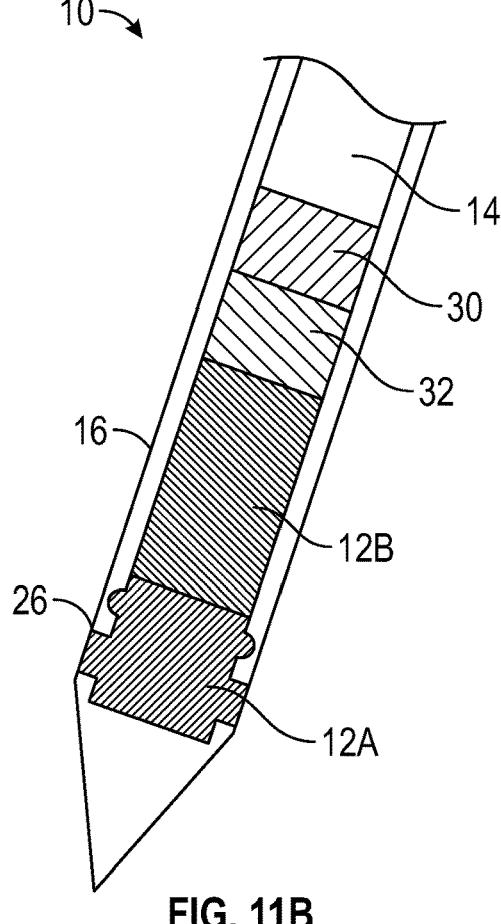
FIG. 11B is a cross-sectional view of the oxygen sensor shown in FIG. 11A in accordance with another embodiment of the present disclosure.

FIGS. 11A-11B show the distal end portion of another embodiment of an oxygen sensor 10, in which FIG. 11A shows a perspective view of oxygen sensor 10 and FIG. 11B shows a cross-sectional view of oxygen sensor 10. In this embodiment, a rigid hollow elongate device 16 has a lumen 14 and holes 26 formed into its side to allow oxygen equilibration between the outside and interior of the elongate device 16. The holes 26, lumen 14, or both may be filled with solid-state contrast agent 12. The holes 26 and distal end portion of the lumen 14 are filled with two layers of material 12A and 12B. The layer 12A may be either elastomeric silicone or the solid-state contrast agent that is a different formula than the second layer 12B of solid-state contrast agent. Layer 12A may be of a higher viscosity than that of layer 12B to prevent the loss of silicone from the holes prior to curing. Alternatively, layers of 12A and 12B may be the same formulation of solid-state contrast agent and dispensed simultaneously. A rigid plug 32 is used to distribute load across the solid-state contrast agent layer 12B. An epoxy layer 30 is used seal the solid-state contrast agent layer(s) 12A-B from the inner lumen 14 of the catheter which may be exposed to the environment outside the body. This ensures only oxygen diffusing from the tissue influences the oxygen measurement. In alternative embodiments, the rigid plug 32 may be omitted, and the epoxy 30 may be in direct contact with the solid-state contrast agent 12B. The epoxy 30 may be a material that has low oxygen solubility or a low oxygen diffusivity.

Brachytherapy Systems and Methods

Improved brachytherapy systems and methods are provided for use in treating cancer. For example, the improvement relates to measuring tumor oxygen levels in order to provide timely adjustments to improve dosing and targeting of elevated doses of radiation to the tumor. In some embodiments, the brachytherapy system can include an alignment template, one or more oxygen sensors, optionally one or more applicators for delivering a radiation source, radioactive source, and a remote after loader. A brachytherapy system, or a portion thereof, can be deployable adjacent to a tissue site of a patient or inside a tissue site of a patient. A brachytherapy system, or a portion thereof, can be implantable within a patient. A brachytherapy system can be used to take repeated measurements of dissolved oxygen levels at a tissue site and selectively administer doses of radiation therapy.

A brachytherapy system may be deployed or implanted in a patient's cervix, prostate, breast, skin, brain, eye, head and neck region (e.g., lip, floor of mouth, tongue, nasopharynx and oropharynx), respiratory tract (e.g., trachea and bronchi), digestive tract (e.g., esophagus, gall bladder, bile-ducts, rectum, anus), urinary tract (e.g., bladder, urethra, penis), female reproductive tract (e.g. uterus, vagina, vulva), or soft tissues, and may be sized and shaped for deployment and/or implantation at any of these tissue sites.

A brachytherapy system may include an alignment template. An alignment template can facilitate the deployment and insertion of oxygen sensors and/or applicators in a patient. An alignment template typically has a grid including rows and columns of holes, for example 5-15 rows and columns, spaced apart a fixed distance, such as 2 mm to 2 cm apart, and dimensioned to accept oxygen sensors and applicators. The grid enables accurate placement of oxygen sensors and applicators in a predefined area of a patient's tissue, the precise spatial measurement and mapping of tissue oxygen concentrations in the patient's tissue, and the precise delivery of radiation therapy to the patient's tissue. An alignment template may also have a tandem channel. The alignment template may include fasteners, such as collets, that securely hold in place any oxygen sensors and applicators disposed in holes of the alignment template. An alignment template can be made of MRI-compatible materials, such as a plastic materials like polyphenylsulfone.

A brachytherapy system may include one or more oxygen sensors. An oxygen sensor can be used to take repeated measurements of dissolved oxygen levels at a tissue site and, optionally, to deliver a radiation source when the oxygen sensor has a channel dimensioned to receive a radiation source.

A brachytherapy system may include one or more applicators. An applicator is configured to deliver a radiation source, and is typically a needle or plastic catheter. An applicator may be made from materials similar to those used in oxygen sensors.

One or more oxygen sensors and/or one or more applicators may be inserted through the template grid holes of an alignment template and securely held in place by fasteners or an interference fit. In some embodiments, a brachytherapy system includes between 3-25 oxygen sensors and/or 3-25 applicators. In some embodiments, a brachytherapy system includes 3, 4, 5, 6, 7, 8, 9, 10, 11, 12, 13, 14, 15, 16, 17, 18, 19, 20, 21, 22, 23, 24, or 25 oxygen sensors, or any ranges thereof. In some embodiments, a brachytherapy system includes 3, 4, 5, 6, 7, 8, 9, 10, 11, 12, 13, 14, 15, 16, 17, 18, 19, 20, 21, 22, 23, 24, or 25 applicators, or any ranges thereof.

In embodiments, a brachytherapy system includes oxygen sensors, but not applicators, because the oxygen sensors are configured to deliver a radiation source. In embodiments, a brachytherapy system includes oxygen sensors, which may or may not be configured to deliver a radiation source, as well as applicators configured to deliver a radiation source. In these embodiments, the oxygen sensors may be placed near one or more applicators to map tissue oxygen concentration near radiation sites.

Figure 8A:
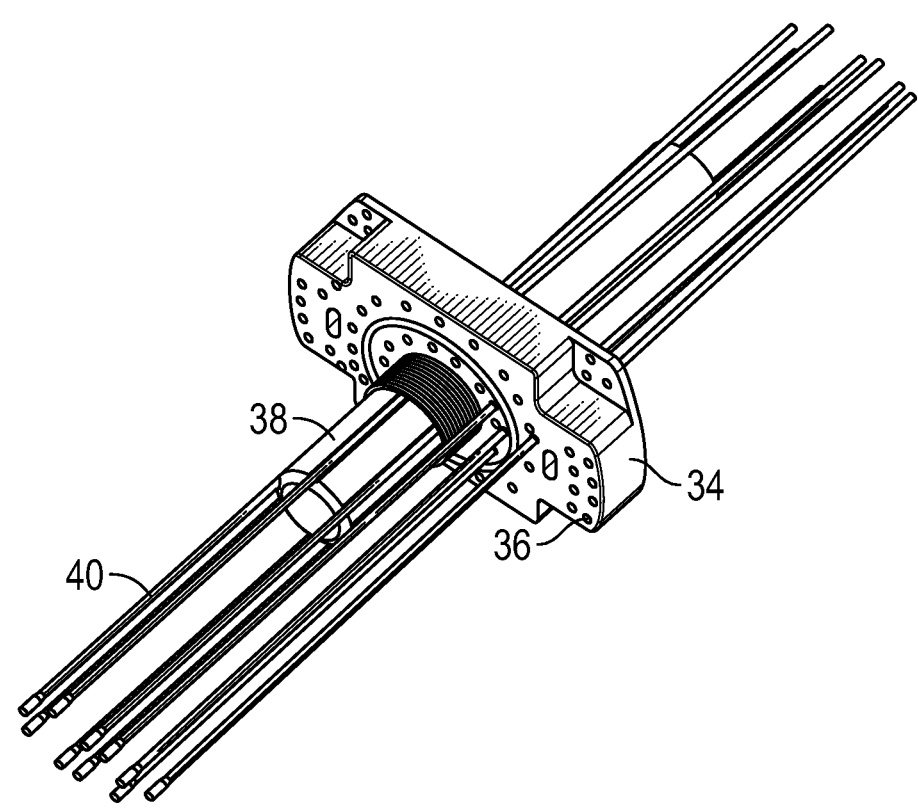
FIG. 8A is a perspective view of an alignment template with a plurality of catheters extending therethrough, in accordance with one embodiment of the present disclosure.
Figure 8B:
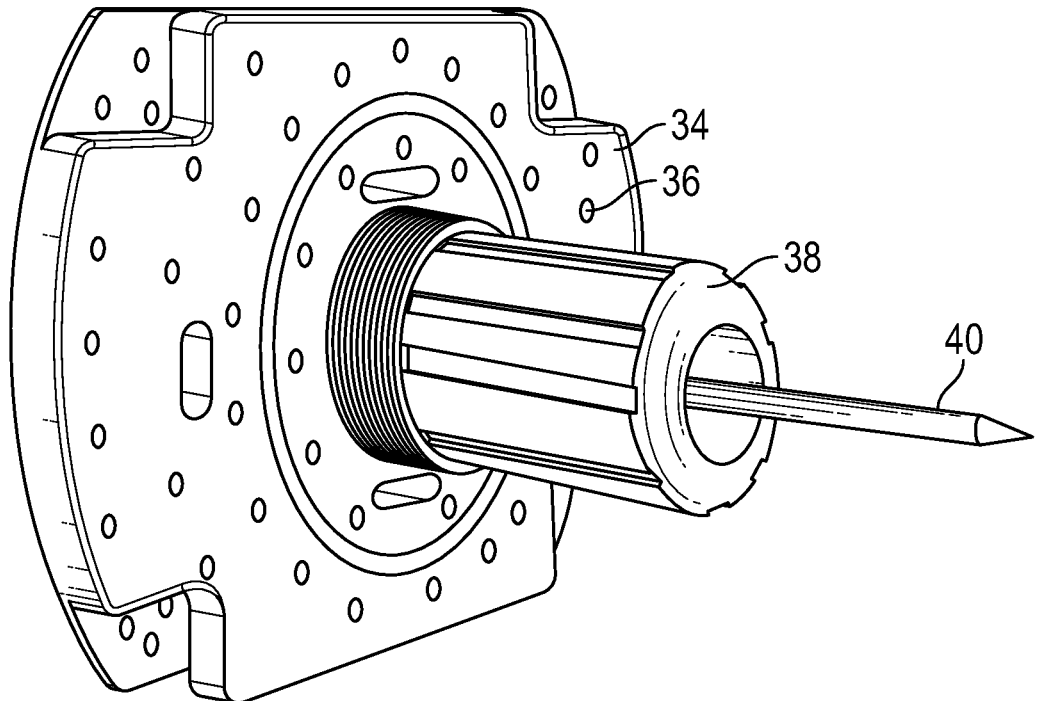
FIG. 8B is a perspective view of a silicone catheter placed in a tandem channel of an alignment template, in accordance with one embodiment of the present disclosure.

FIGS. 8A-8B show embodiments of a brachytherapy system. FIG. 8A shows a brachytherapy alignment template 34 and catheters 40. The brachytherapy alignment template 34 includes a plurality of small holes 36 positioned across the surface of the template, each hole extending through the template and dimensioned to accept a catheter 40. The brachytherapy alignment template 34 also includes a tandem channel 38 extending through the center of alignment template 34. Catheters 40, which may be oxygen sensors, applicators, or a combination thereof, are disposed in small holes 36. FIG. 8B shows a brachytherapy alignment template 34 with a single catheter 40 inserted through a tandem channel 38 that corresponds with the location of a pre-created needle path. The catheter 40 is a silicone-catheter based oxygen sensor. Alternatively, a non-silicone based oxygen sensor could be used.

Methods of Use

Provided are methods for monitoring, in vivo or ex vivo, tissue oxygenation in a patient and methods for treating a tumor in a patient. The methods for treatment incorporate the methods for monitoring tissue oxygenation, but include additional steps for adaptive brachytherapy based on measured tumor tissue oxygenation levels. Thus, the methods include mapping tissue oxygen levels in a patient using one or more oxygen sensors to determine a tissue oxygenation profile of a tumor and surrounding tissues in the patient, and then optionally performing adaptive brachytherapy to treat the tumor based at least in part on the measured oxygen concentration profiles. The methods can generally include (i) deploying one or more oxygen sensors, one or more applicators, and/or a brachytherapy system at a tissue site of a patient, (ii) subjecting the tissue site to electromagnetic radiation, (iii) assessing the MRI relaxation time ($T_1$) of protons in the oxygen sensors using magnetic resonance based imaging, (iv) determining a dissolved oxygen concentration profile of the tissue site by converting the measured relaxation times to an oxygen partial pressure based on a predetermined, application independent, calibration curve, (v) optionally administering radiation sources via the oxygen sensors and/or applicators, which may or may not be disposed in an alignment template, to the tissue site based on the determined dissolved oxygen concentration profile of the tissue site, and (vi) optionally repeating steps some or all of steps (ii)-(v).

In embodiments, a MRI scan is performed prior to deploying and/or inserting one or more oxygen sensors, one or more applicators, and/or a brachytherapy system at a specific target tissue site of interest. The MRI scan may be used to visualize the shape and size of the target tissue site (e.g. a tumor and surrounding tissue) to develop a preliminary brachytherapy treatment plan.

In embodiments, the methods include directly deploying and/or inserting one or more oxygen sensors, one or more applicators, and/or a brachytherapy system under MRI guidance at a specific target tissue site of interest (e.g. a tumor and surrounding tissue), based on the preliminary brachytherapy treatment plan, to allow for site-specific measurement, analysis, and treatment of the tissue site. In embodiments, the methods include directly deploying and/or inserting one or more oxygen sensors, one or more applicators, and/or a brachytherapy in and about a tumor in a patient. The use of MRI guidance can help direct the one or more oxygen sensors, one or more applicators, and/or a brachytherapy system to their correct positions and ensure that they are placed in the most effective location. In embodiments, the methods include deploying and/or inserting one or more oxygen sensors, one or more applicators, and/or a brachytherapy system in a patient's cervix, prostate, breast, skin, brain, eye, head and neck region (e.g., lip, floor of mouth, tongue, nasopharynx and oropharynx), respiratory tract (e.g., trachea and bronchi), digestive tract (e.g., esophagus, gall bladder, bile-ducts, rectum, anus), urinary tract (e.g., bladder, urethra, penis), female reproductive tract (e.g. uterus, vagina, vulva), or soft tissues, for the purpose of measuring tissue oxygenation levels and/or treating cancers of these tissues.

In embodiments, once the one or more oxygen sensors, one or more applicators, and/or a brachytherapy system are deployed in the correct position, further imaging and analysis can be performed to refine the preliminary brachytherapy treatment plan. This can include performing a MRI scan to precisely contour tissue structures and/or determine a profile of tumor oxygen levels. In embodiments, this can include subjecting a tissue site to electromagnetic radiation, assessing the MRI relaxation time ($T_1$) of protons in the oxygen sensors using magnetic resonance based imaging, and determining a dissolved oxygen concentration profile of the tissue site by converting the measured relaxation times to an oxygen partial pressure based on a predetermined, application independent, calibration curve.

A clinician may refine the preliminary treatment plan by determining an optimal spatial and temporal distribution of radiation sources based on the measured tissue oxygenation profiles of a tumor in a patient. Refining the treatment plan can help avoid delivering too little or too much irradiation, which can respectively cause treatment failure and side effects, to any region of a tumor during treatment. Refining the treatment plan can help ensure that the whole tumor receives an optimal level of radiation by tailoring the radiation doses delivered to different regions of a tumor. Refining the treatment plan can include adjusting the placement of source carriers, selecting a subset of source carriers to deliver a radiation source based on their position within a tissue, and/or adjusting the radiation dose delivered by each source carrier (e.g. exposure time to a radiation source). In embodiments, refining the treatment plan allows a clinician to compensate for the desensitization of tumors to radiation treatment in regions with lower oxygen content by selectively increasing radiation doses, thereby improving cancer outcomes in patients treated with MRI-guided brachytherapy. For example, tumor sub-volumes determined to be hypoxic may require radiation dose escalation for effective therapy, and a clinician may adjust the delivery of radiation sources at the tissue site such that more radiation sources are delivered proximate to the tumor and/or selectively increase radiation doses delivered by specific radiation source carriers.

In embodiments, the methods include performing brachytherapy by administering radiation sources to the tissue site according to the refined treatment plan. The brachytherapy may include temporarily and precisely placing short-range radiation sources (e.g., radioisotopes) either on or within body tissues or cavities, and directly at the site of a tumor, for a set duration of time effective to treat a tumor before being withdrawn. A radioactive source may be contained within a needle, seed, wire, or catheter that may be placed directly into a tumor or tumor bed temporarily or permanently. The brachytherapy may be interstitial brachytherapy where radiation sources are placed directly in a target tissue of an affected site, e.g. a site with a tumor. The brachytherapy may be contact brachytherapy where radiation sources are placed in a space next to the target tissue, such as a body cavity (e.g. cervix, uterus or vagina), a body lumen (e.g. trachea or esophagus), or externally (e.g. the skin).

In embodiments, the brachytherapy may include delivering a high dose of localized radiation to a small tumor area while sparing surrounding healthy tissue. The brachytherapy may deliver radiation sources (radionuclides) such as, for example, cesium-131, cesium-137, cobalt-60, iridium-192, iodine-125, palladium-103, ruthenium-106, and radium-226. The brachytherapy may be high dose rate (HDR) brachytherapy characterized by a high rate of dose delivery that exceeds 12 Gy/h. The brachytherapy may be medium-dose rate (MDR) brachytherapy characterized by a medium dose rate of dose delivery, ranging between 2 Gy/h to 12 Gy/h.

The brachytherapy may be low-dose rate (LDR) brachytherapy characterized by a low rate of dose delivery that is below 2 Gy/h.

The duration of a single brachytherapy treatment will depend on many different factors, including the required rate of dose delivery and the type, size, and location of the tumor. Typical durations for delivering a single dose of radiation range from minutes to hours. For example, HDR brachytherapy utilizes high intensity sources to deliver a radiation dose over a short period of time, for example in about two to twenty minutes, whereas LDR brachytherapy utilizes low intensity sources to deliver a radiation dose over a long period of time, for example up to 24 hours.

In embodiments, the methods for monitoring, in vivo or ex vivo, tissue oxygenation in a patient and the methods for treating a tumor in a patient are based on adaptive planning, and some or all of the method steps may be repeated.

For example, the one or more oxygen sensors can be subjected to repeated measurements to monitor shifts in tissue oxygen concentration profiles over time. An initial measurement of each oxygen sensor may be made immediately following placement. Follow-up measurements may be made immediately prior to each brachytherapy session such that the brachytherapy plan can be adjusted according to the hypoxia of tumor sub-volumes. Additional measurements may be made at other time points during or following treatment when information about the tissue oxygen content is useful to clinicians. In embodiments, 1, 2, 3, 4, 5, 6, 7, 8, 9, or 10 temporally spaced oxygen measurements, or any ranges thereof, are made over the course of a complete brachytherapy treatment.

As another example, radiation sources may be delivered in two or more fractions over one to several treatment sessions per day for several days. Each treatment session may be separated from other treatment sessions by a non-treatment period ranging from, for example, 3-24 hours. In one exemplary embodiment, 1-6 HDR brachytherapy treatments, separated by at least non-treatment periods of 6 hours, are delivered over one to three days. The brachytherapy dose distribution in each fraction may be modified in response to measured tumor oxygen content by adjusting the relative positioning of radiation sources as well as the exposure time to each radiation source. With this inherent flexibility in dose delivery by brachytherapy, radiation doses can be increased in regions of hypoxia relative to well-oxygenated tumor, while respecting established dose constraints to the adjacent organs.

In embodiments, the methods include deploying a RF coil near a tissue site of a patient, leaving the coil near the tissue site during electromagnetic radiation and MRI imaging of the tissue site, and then removing the coil. A RF coil may be deployed through or in a channel in an oxygen sensor or a nearby applicator. A RF coil may be an endorectal coil used with MRI for imaging of tissues, such as the cervix and prostate, that are near the rectally inserted coil. A RF coil may speed up magnetic resonance measurements and improve locating the one or more oxygen sensors, one or more applicators, and/or a brachytherapy system in vivo. A RF coil may improve spatial resolution and reduce misleading artifacts, resulting in better quality magnetic resonance images. A RF coil may be used for high-resolution imaging of tissues and may significantly reduce the required acquisition time for measuring solid-state contrast agent, which in turn may more quickly provide tumor oxygen level information to the clinician.

In one example, an oxygen sensor having solid-state contrast agent disposed in a clinically approved catheter, such as a 6 French brachytherapy catheter or a 8 French silicone catheter, would be provided. The catheter serves to mechanically isolate the solid-state contrast agent from a patient while still allowing exchange of oxygen between the tissue and the solid-state contrast agent. The solid-state contrast agent would be measured in vivo using a clinical MRI scanner with clinical pulse sequences to determine tissue oxygen concentrations. The measured tissue oxygen concentrations can be used to improve cancer outcomes for patients in a wide variety of cancers including prostate cancer, vaginal recurrence of endometrial cancer, or primary vaginal cancer when treated with MR-guided brachytherapy. The MR-guided brachytherapy can be optimized to overcome hypoxia-mediated radiation resistance to improve local tumor control and improve therapeutic outcome post-intervention.

Figure 9:
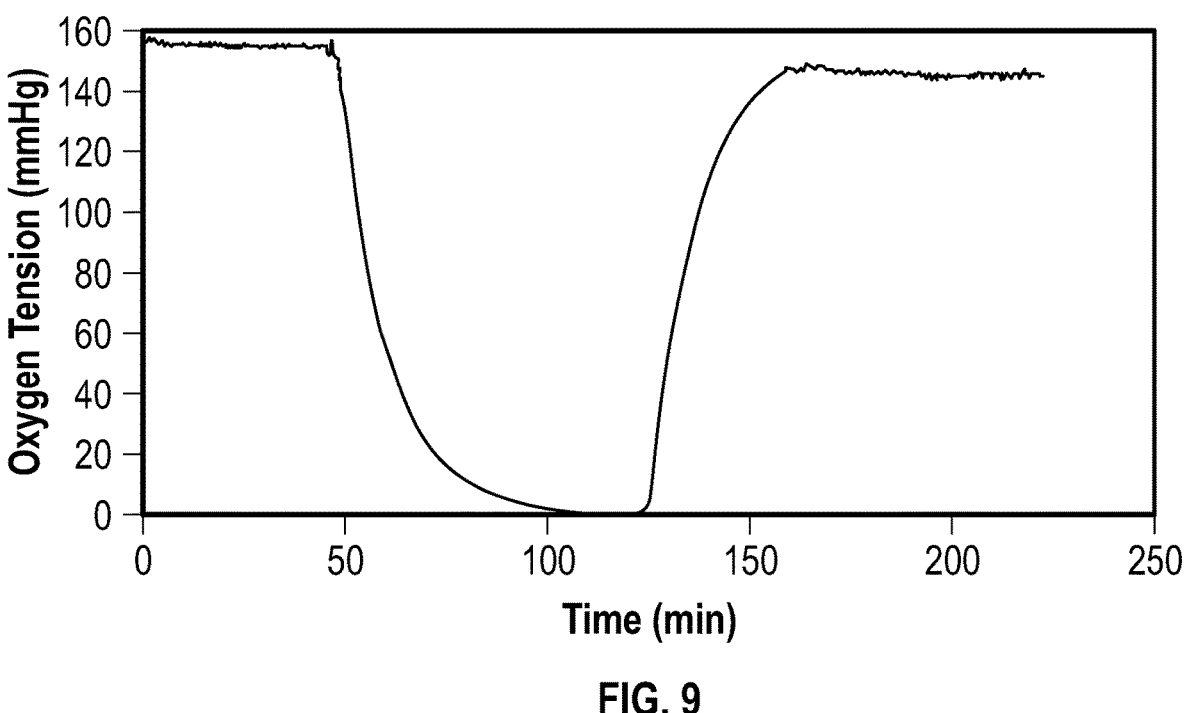
FIG. 9 is a graph depicting a response rate of an oxygen sensor to changes in the oxygen content of the oxygen sensor's surrounding environment, in accordance with one embodiment of the present disclosure.

In one embodiment, an oxygen sensor can be placed, measured, and removed within a limited period without interruption of a normal brachytherapy treatment schedule by piggybacking on the use of MRI to place applicators (e.g., catheters) in conventional brachytherapy. In one embodiment, solid-state contrast agent is completely contained within a clinically approved silicone catheter and the catheter is placed in a tumor at the beginning of a brachytherapy session, enabling multiple measurements of tissue oxygen levels in the tumor and surrounding tissue (3-5 oxygen measurements can be made while the patient is in the scanner). The catheter can be inserted through a tandem channel in an alignment template that corresponds with the location of a pre-created needle path. The tandem channel is frequently unused, and can provide a path to insert a catheter containing a solid-state contrast agent. During the placement process, a metal obturator can be inserted in the catheter to provide rigidity. A standard obturator can be modified (or a smaller diameter one can be created) to enable use of a minimally-sized catheter. The obturator can then be removed from the catheter. The silicone catheter allows transfer of oxygen between the tissue surrounding the catheter and the solid-state contrast agent inside the catheter on a timescale that allows for equilibration during a single imaging session (FIG. 9).

Example 1

A study was conducted to show that a solid-state contrast agent can re-equilibrate when the oxygen content is changed from 0 mmHg (0% O2) to 160 mmHg (21% O2) in under 10 minutes, as illustrated in FIG. 1. The rapid response can be used to measure acute hypoxia within a tumor.

Example 2

Figure 2:
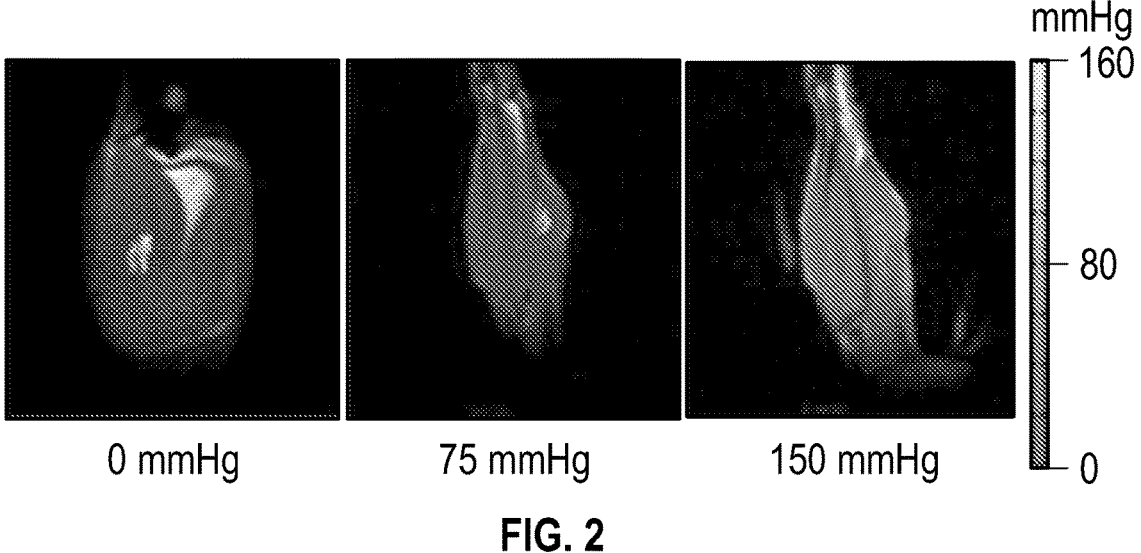
FIG. 2 depicts an oxygen sensor's in vivo measurement of tissue oxygen level changes resulting from changes in inspired gas from oxygen to air.
Figure 3:
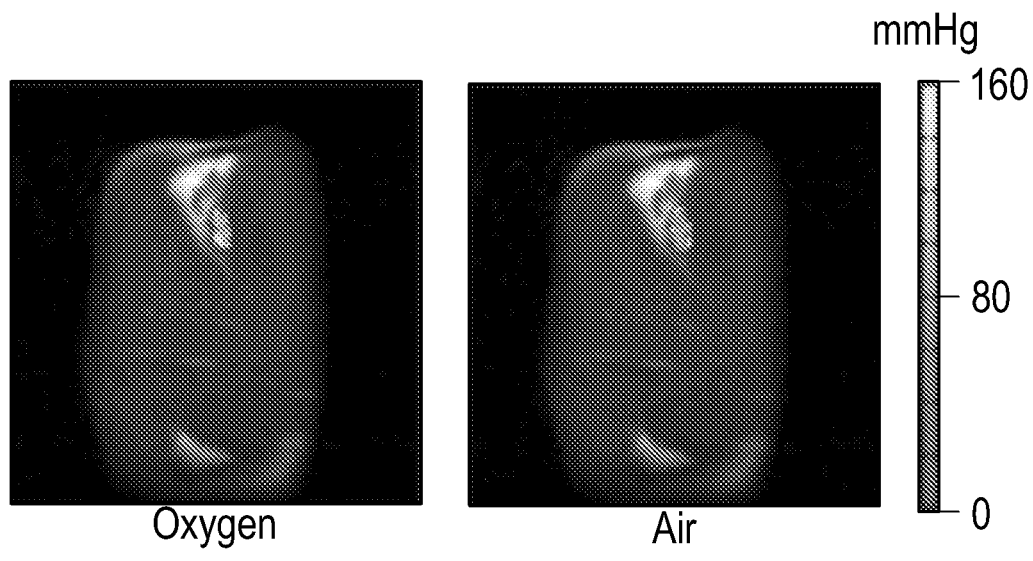
FIG. 3 depicts an oxygen sensor's in vivo measurement of tissue oxygen content changes when a pressure cuff was used to limit blood flow to the limb of a rat.

The liquid phase silicone and silicone elastomer matrix materials have been evaluated in vivo in multiple animal models. In one case, this type of solid-state contrast agent was observed to track changes in tissue oxygen level, in vivo, resulting from changes in the inspired gas from oxygen to air (FIG. 2). As shown in FIG. 2, the measured oxygen partial pressure decreases as the pressure increases from the 0 mmHg to 150 mmHg. The same embodiment of solid-state contrast agent also tracked changes in tissue oxygen content when a pressure cuff was used to limit blood flow to the limb of a rat (FIG. 3) that contained the injected solid-state contrast agent. As shown in FIG. 3, the measured oxygen partial pressure decreases as the inspired gas is transitioned from oxygen to air.

20

Example 3

Figure 10:
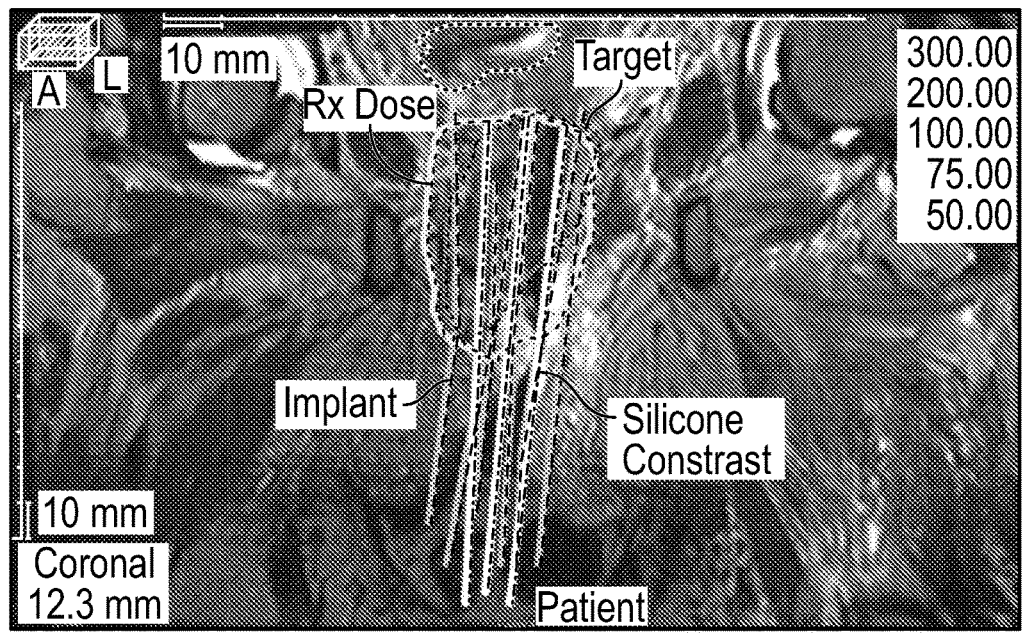
FIG. 10 is an image depicting a plurality of oxygen sensors inserted into a target tissue site in close proximity to and among a plurality of brachytherapy implants inserted into the target tissue.

FIG. 10 shows an image of a plurality of oxygen sensors including solid-state contrast agent inserted into a target tissue site in close proximity to and among a plurality of brachytherapy implants inserted into the target tissue.

Example 4

Figure 12:
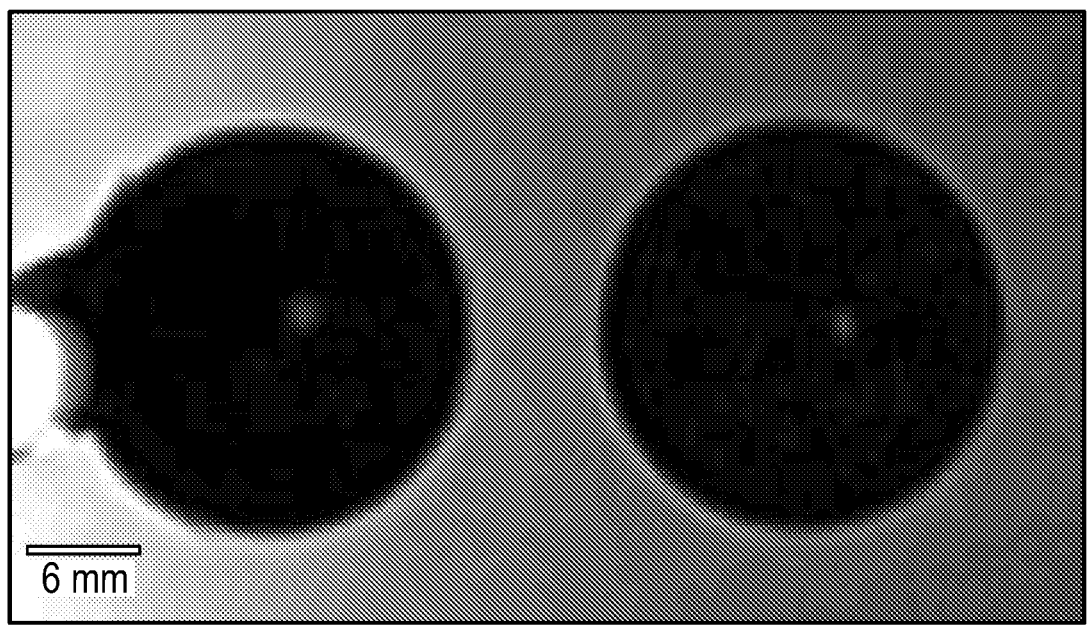
FIG. 12 is MRI scan of a pair of oxygen sensors.

FIG. 12 shows two oxygen sensors (containing the solid-state contrast agent) imaged on a clinical MRI. The oxygen sensors imaged in FIG. 12 were configured with a single row of four machined holes (each 0.020" diameter) spaced on mutually perpendicular surfaces. Their positioning along the length of the sensor corresponds with holes in the bottom row of FIG. 11A. The layer 12A was about 1.5 mm thick and the layer 12B was about 2 mm thick. The 12A layer was dispensed pre-cured. The 12B layer was cured before being inserted into the lumen of the sensor. The formulation of silicone used for 12A was 20% of 100 cP silicone oil and 80% pre-cured silicone elastomer with properties of 25,500 cP and durometer 75 type A based on a weight/weight percentage. A dye suitable for modifying the color of silicone materials was added at 2% of the total weight of the silicone oil and elastomer combined. All components were in a single vessel during mixing. The dye made inspection of the 12A layer easier. The formulation of silicone used for 12B was 70% of 100 cP silicone oil and 30% pre-cured silicone elastomer with properties of 25,500 cP and durometer 75 type A based on a weight/weight percentage. These formulations were cured at 50° C. for 2 hours. The delrin plug was inserted following the insertion of the 12B layer. A light-cure acrylic epoxy was dispensed on top of the delrin plug. The epoxy was then cured using a 405 nm wavelength light source at 100% for two seconds. This was repeated on the three remaining mutually perpendicular surfaces.

Example 5

Another version of the sensor was produced in a manner similar to Example 4. The differences included additional holes, two rows of six holes each as shown in FIG. 11A. The 12A was about 2 mm thick and the 12B layer was about 5 mm thick.

The sensor was measured using the same 3 Tesla clinical MRI utilizing an inversion recovery pulse sequence. This sensor was measured with inversion times of 24, 50, 80, 108, 146, 198, 268, 363, 490, 663, 896, 1640, 2200, and 2800 ms. The data was collected using the spine coil, body-matrix coil, and the endorectal coil. The data was collected using a slice thickness of 2 mm, a repetition time of 3000 ms, and an echo time of 15 ms. The intensity values were extracted using Matlab, and the data was fit to the inversion recovery equation to extract the $T_1$ value. When imaged in an environment with 21% oxygen, the sensor had a relaxation time $(T_1)$ of about 620 ms. When imaged in an environment with 0% oxygen, the sensor had a relaxation time $(T_1)$ of about 750 ms. This relaxation time may be modified by selecting a different liquid component for the solid-state contrast agent formulation.

Modifications and variations of the methods and devices described herein will be obvious to those skilled in the art from the foregoing detailed description. Such modifications and variations are intended to come within the scope of the appended claims.

We claim:

1. A method for monitoring in vivo tumor oxygenation in a patient, the method comprising:

inserting at least one oxygen sensor unit, which comprises a catheter and a first quantity of a solid-state contrast agent for oxygen, into a first selected subvolume of a tumor located within the patient;

using magnetic resonance (MR) to assess an MR property of the at least one oxygen sensor unit; and quantifying an oxygen level in the first selected subvolume of the tumor, based on the assessed MR property and a calibration curve;

wherein the first quantity of the solid-state contrast agent for oxygen (i) is disposed and secured on an outer surface of the catheter, or (ii) is disposed and secured in an interior volume of the catheter when a portion of the outer surface of the catheter is oxygen permeable or comprises a path for oxygen diffusion, and wherein the solid-state contrast agent for oxygen comprises a liquid phase silicone dispersed in a chemically cross-linked silicone elastomer matrix.

2. The method of claim 1, wherein the MR property is a MR relaxation time (T1) of protons in the at least one oxygen sensor unit.

3. The method of claim 1, wherein the catheter comprises an oxygen-permeable annular tube in which the first quantity of the solid-state contrast agent for oxygen is disposed and secured, and the annular tube comprises (i) a side wall that is substantially impermeable to oxygen, and (ii) one or more apertures through a distal end region of the sidewall through which oxygen can diffuse to reach the solid-state contrast agent.

4. The method of claim 1, wherein the catheter comprises a rigid body having the outer surface onto which the first quantity of the solid-state contrast agent for oxygen is disposed and secured, the rigid body including an internal channel configured to receive a radiation source and/or to accept a coil for making an MR measurement.

5. The method of claim 1, wherein the catheter of the at least one oxygen sensor unit comprises multiple, discrete quantities of the solid-state contrast agent for oxygen.

6. The method of claim 1, further comprising inserting a second oxygen sensor unit into a second selected subvolume of the tumor, the first and second subvolumes being different volumes from one another, wherein the second oxygen sensor unit comprises a second quantity of the solid-state contrast agent for oxygen.

7. The method of claim 6, wherein the second oxygen sensor unit comprises a second catheter on or in which the second quantity of the solid-state contrast agent for oxygen is fixed.

8. The method of claim 1, wherein the catheter is an annular tube having an internal channel extending therethrough dimensioned to receive (i) a radiation source and/or (ii) a coil for making a MR measurement.

9. The method of claim 1, wherein:

magnetic resonance imaging is used to assess a MR relaxation time (T1) of protons in the at least one oxygen sensor unit;

the quantifying of the oxygen level in the first selected subvolume of the tumor is based on the assessed MR relaxation time and the calibration curve; and the quantified oxygen level in the first selected subvolume of the tumor is used to select or adjust delivery of a high dose rate brachytherapy to the tumor.

10. A method of treating a solid tumor in a patient, the method comprising:

selectively placing a plurality of oxygen sensor units, comprising a catheter and a solid-state contrast agent for oxygen, directly into the tumor or tissues surrounding the tumor;

selectively placing a plurality of radiation source catheters directly into the tumor or tissues surrounding the tumor to deliver high dose rate brachytherapy; and measuring oxygen levels about the solid-state contrast agent for oxygen, using MRI to assess an MR relaxation time (T1) of protons in the solid-state contrast agent for oxygen, wherein said measuring is conducted before, during, and/or after the high dose rate brachytherapy;

wherein the solid-state contrast agent for oxygen (i) is disposed and secured on an outer surface of the catheter, or (ii) is disposed and secured in an interior volume of the catheter when a portion of the outer surface of the catheter is oxygen permeable or comprises a path for oxygen diffusion, and wherein the solid-state contrast agent for oxygen comprises a liquid phase silicone dispersed in a chemically cross-linked silicone elastomer matrix.

11. The method of claim 10, wherein the dose of the high dose rate brachytherapy is adjusted based on a measured (i) hypoxia of a tumor sub-volume, (ii) higher than average oxygen content of a tumor sub-volume, to be less in the tumor sub-volume than an average dose for the tumor, or (iii) lower than average oxygen content of a tumor sub-volume, to be more in the tumor sub-volume than an average dose for the tumor.

12. The method of claim 11, wherein the dose of the high dose rate brachytherapy is adjusted based on the measured hypoxia of the tumor subvolume, and the adjustment comprises altering a relative position or time of a radiation source within one or more of the plurality of radiation source catheters, in order to increase the radiation dose in the tumor sub-volume in which hypoxia is measured.

13. The method of claim 10, wherein the patient has been diagnosed with cervical cancer, prostate cancer, endometrial cancer, or primary vaginal cancer, and wherein the solid tumor is associated with the diagnosed cancer.

14. A medical device for monitoring in vivo tissue oxygenation comprising:

a catheter having at least a distal end portion configured for insertion into tissue within a patient; and one or more units of a solid-state contrast agent for oxygen sensing, wherein the catheter comprises (i) an oxygen-permeable annular tube in which the one or more units of the solid-state contrast agent for oxygen sensing are disposed and secured, (ii) an annular tube in which a portion is oxygen permeable in which the one or more units of a solid-state contrast agent for oxygen sensing are disposed and secured, (iii) an outer surface onto which the one or more units of a solid-state contrast agent for oxygen sensing are fixed and secured, or (iv) a combination of (i), (ii), and (iii), and wherein the solid-state contrast agent for oxygen comprises a liquid phase silicone dispersed in a chemically cross-linked silicone elastomer matrix.

15. The medical device of claim 14, which has two or more units of the solid-state contrast agent for oxygen sensing and the two or more units are spaced apart from one another by at least 1 mm.

16. A system for treating a solid tumor in a patient comprising:

an alignment template having a plurality of holes; and two or more oxygen sensor units, wherein each oxygen sensor unit (i) comprises one or more units of a solid-state contrast agent for oxygen sensing, (ii) is a catheter having at least a distal end portion configured for insertion into tissue within a patient, and (iii) is configured for passage through a respective one of the plurality of holes;

wherein the solid-state contrast agent for oxygen (i) is disposed and secured on an outer surface of the catheter, or (ii) is disposed and secured in an interior volume of the catheter when a portion of the outer surface of the catheter is oxygen permeable or comprises a path for oxygen diffusion, and wherein the solid-state contrast agent for oxygen comprises a liquid phase silicone dispersed in a chemically cross-linked silicone elastomer matrix.

17. The system of claim 16, further comprising:

one or more applicators, wherein each applicator (i) is configured to deliver a radiation source, (ii) has at least a distal end portion configured for insertion into tissue within the patient, and (iii) is configured for passage through a respective one of the plurality of holes.

18. A method for monitoring in vivo tumor oxygenation in a patient, the method comprising:

inserting at least one oxygen sensor unit, which comprises a catheter and a first quantity of a solid-state contrast agent for oxygen, into a first selected subvolume of a tumor located within the patient;

using MR to assess a MR relaxation time of protons in the at least one oxygen sensor unit;

determining a quantitative reference point for a qualitative oxygen evaluation method; and determining, based at least in part on the quantitative reference point, quantitative oxygen levels in one or more subvolumes of the tumor measured with the qualitative oxygen evaluation method;

wherein the solid-state contrast agent for oxygen (i) is disposed and secured on an outer surface of the catheter, or (ii) is disposed and secured in an interior volume of the catheter when a portion of the outer surface of the catheter is oxygen permeable or comprises a path for oxygen diffusion, and wherein the solid-state contrast agent for oxygen comprises a liquid phase silicone dispersed in a chemically cross-linked silicone elastomer matrix.

19. The method of claim 18, wherein the qualitative oxygen evaluation method is blood oxygen dependent MRI based or positron emission tomography based.

* * * * *